United States Patent [19]

Lu et al.

[11] Patent Number: 5,731,317
[45] Date of Patent: Mar. 24, 1998

[54] BRIDGED PIPERIDINES PROMOTE RELEASE OF GROWTH HORMONE

[75] Inventors: Zhijian Lu, Scotch Plains; Arthur A. Patchett; James R. Tata, both of Westfield, all of N.J.

[73] Assignee: Merck & Co., Inc., Rahway, N.J.

[21] Appl. No.: 401,849

[22] Filed: Mar. 10, 1995

[51] Int. Cl.$^6$ .......................... A61K 31/445; A61K 31/46
[52] U.S. Cl. ........................... 514/289; 514/284; 546/71; 546/72; 546/73; 546/74
[58] Field of Search ....................... 546/125, 129, 546/130, 131, 132, 1, 26, 61, 71, 72, 73, 74, 77; 514/289, 284, 279, 278, 277, 294

[56] References Cited

U.S. PATENT DOCUMENTS

| | | | |
|---|---|---|---|
| 3,239,345 | 3/1966 | Hodge et al. | |
| 4,036,979 | 7/1977 | Asato | 424/275 |
| 4,411,890 | 10/1983 | Momany | 424/177 |
| 4,782,139 | 11/1988 | DiMarchi et al. | 530/407 |
| 5,137,872 | 8/1992 | Seely et al. | 514/12 |
| 5,164,368 | 11/1992 | Recker | 514/12 |
| 5,206,235 | 4/1993 | Fisher et al. | 514/213 |
| 5,242,927 | 9/1993 | Baker et al. | 546/125 |
| 5,283,241 | 2/1994 | Bochis et al. | 514/183 |
| 5,284,841 | 2/1994 | Chu et al. | 514/183 |
| 5,310,737 | 5/1994 | Fisher et al. | 514/215 |
| 5,317,017 | 5/1994 | Ok et al. | 514/211 |
| 5,391,742 | 2/1995 | Chenard | 546/125 |
| 5,578,593 | 11/1996 | Chen et al. | 514/278 |

FOREIGN PATENT DOCUMENTS

| | | |
|---|---|---|
| 0 144 230 A3 | 6/1985 | European Pat. Off. |
| 5163224 | 6/1993 | Japan |
| WO 94/07486 | 4/1994 | WIPO |
| WO 94/08583 | 4/1994 | WIPO |
| WO 94/13696 | 6/1994 | WIPO |
| WO 94/19367 | 9/1994 | WIPO |
| WO 95/13069 | 5/1995 | WIPO |

OTHER PUBLICATIONS

R.G. Smith, et al., *Science*, Reprint Series, 11 Jun. 1993, vol. 260, pp. 1640–1643 "A Nonpeptidyl Growth Hormone Secretagogue".
Sakamoto, et al., *Chem. Abstracts*, 113(9) 73,560u (1990).
Horwell, et al., *Chem. Abstracts*, 113(15) 132,771p (1990).

*Primary Examiner*—Melvyn I. Marquis
*Assistant Examiner*—Robert H. Harrison
*Attorney, Agent, or Firm*—J. Eric Thies; David L. Rose

[57] ABSTRACT

The present invention is directed to certain novel compounds identified as bridged piperidines of the general structural formula:

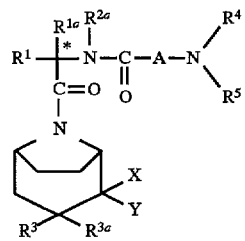

wherein $R^1$, $R^{1a}$, $R^{2a}$, $R^3$, $R^{3a}$, $R^4$, $R^5$, A, X, and Y are as defined herein. These compounds promote the release of growth hormone in humans and animals. This property can be utilized to promote the growth of food animals to render the production of edible meat products more efficient, and in humans, to treat physiological or medical conditions characterized by a deficiency in growth hormone secretion, such as short stature in growth hormone deficient children, and to treat medical conditions which are improved by the anabolic effects of growth hormone. Growth hormone releasing compositions containing such compounds as the active ingredient thereof are also disclosed.

5 Claims, No Drawings

BRIDGED PIPERIDINES PROMOTE RELEASE OF GROWTH HORMONE

BACKGROUND OF THE INVENTION

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy. A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth harmone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recombinant growth hormone has become available which, while no longer carrying any risk of disease transmission, is still a very expensive product which must be given by injection or by a nasal spray. Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. Non peptidal growth hormone secretagogues with a benzolactam structure are disclosed in e.g., U.S. Pat. Nos 5,206,235, 5,283,241, 5,284,841, 5,310,737 and 5,317,017. Other non-peptidal growth hormone secretagogues are disclosed in PCT Patent Publications WO 94/13696 and WO 94/19367. The instant compounds are low molecular weight peptide analogs for promoting the release of growth hormone which have good stability in a variety of physiological environments and which may be administered parenterally, nasally or by the oral route.

SUMMARY OF THE INVENTION

The instant invention is directed to certain bridged piperidine compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the piperidine compounds. It is a further object of this invention to describe procedures for the preparation of such compounds. A still further object is to describe the use of such compounds to increase the secretion of growth hormone in humans and animals. A still further object of this invention is to describe compositions containing the piperidine compounds for the use of treating humans and animals so as to increase the level of growth hormone secretions. Further objects will become apparent from a reading of the following description.

DESCRIPTION OF THE INVENTION

The novel piperidine compounds of the instant invention are best described in the following structural Formula I:

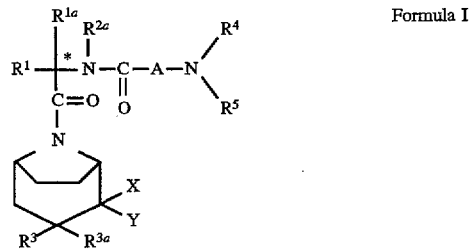

Formula I wherein:

$R^1$ is selected from the group consisting of:
  $C_1$–$C_{10}$ alkyl, aryl, aryl($C_1$–$C_6$ alkyl), ($C_3$–$C_7$ cycloalkyl)($C_1$–$C_6$ alkyl)-, ($C_1$–$C_5$ alkyl)-K—($C_1$–$C_5$ alkyl)-, aryl($C_0$–$C_5$ alkyl)-K—($C_1$–$C_5$ alkyl)-, and ($C_3$–$C_7$ cycloalkyl)($C_0$–$C_5$ alkyl)-K—($C_1$–$C_5$ alkyl)-, where K is —O—, —S(O)$_m$—, —N($R^2$)C(O)—, —C(O)N($R^2$)—, —OC(O)—, —C(O)O—, —$CR^2$=$CR^2$—, or —C≡C—, where aryl is selected from: phenyl, naphthyl, indolyl, quinolinyl, isoquinolinyl, azaindolyl, pyridyl, benzothienyl, benzofuranyl, thiazolyl, and benzimidazolyl, and $R^2$ and alkyl may be further substituted by 1 to 9 halogen, —S(O)$_m R^{2a}$, 1 to 3 of —$OR^{2a}$ or —C(O) $OR^{2a}$, and aryl may be further substituted by 1 to 3 of $C_1$–$C_6$ alkyl, 1 to 3 of halogen, 1 to 2 of —$OR^2$, methylenedioxy, —S(O)$_m R^2$, 1 to 2 of —$CF_3$, —$OCF_3$, nitro, —N($R^2$)C(O)($R^2$), —C(O)$OR^2$, —C(O)N($R^2$)($R^2$), -1H-tetrazol-5-yl, —$SO_2$N($R^2$) ($R^2$), —N($R^2$)$SO_2$ phenyl, or —N($R^2$)$SO_2 R^2$;

$R^{1a}$ is hydrogen, or $C_1$–$C_6$ alkyl optionally substituted by phenyl;

$R^2$ is selected from: hydrogen, $C_1$–$C_6$ alkyl, and $C_3$–$C_7$ cycloalkyl, and where two $C_1$–$C_6$ alkyl groups are present on one atom, they may be optionally joined to form a $C_3$–$C_8$ cyclic ring, optionally including oxygen, sulfur or $NR^{3a}$;

$R^{2a}$ is hydrogen, or $C_1$–$C_6$ alkyl optionally substituted by phenyl;

$R^3$ is hydrogen, or —(CH$_2$)$_t$aryl wherein aryl is selected from the group consisting of:

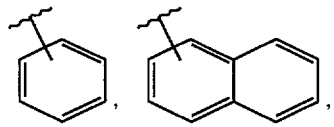

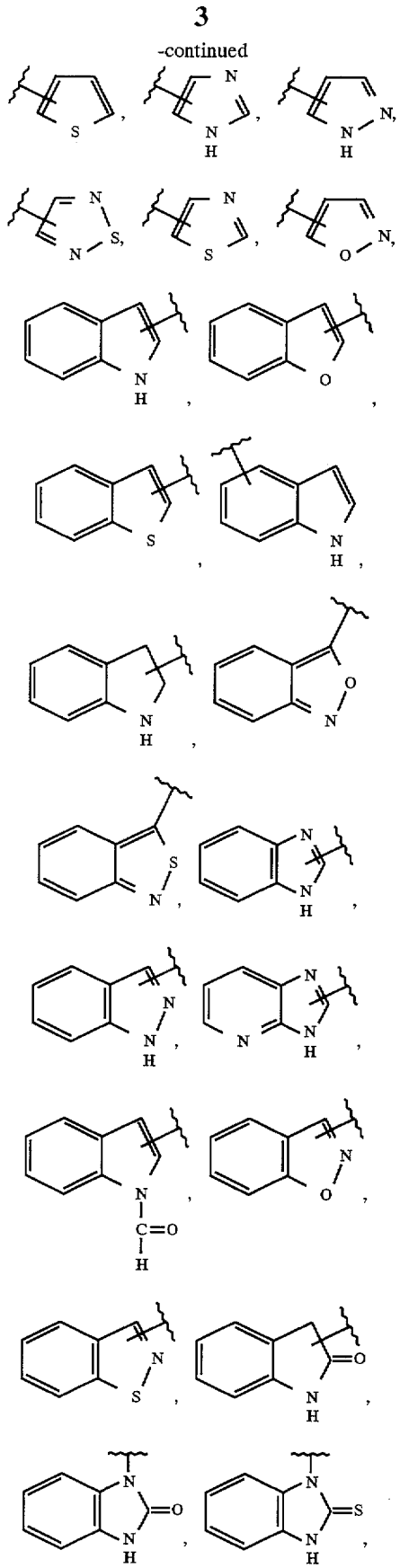

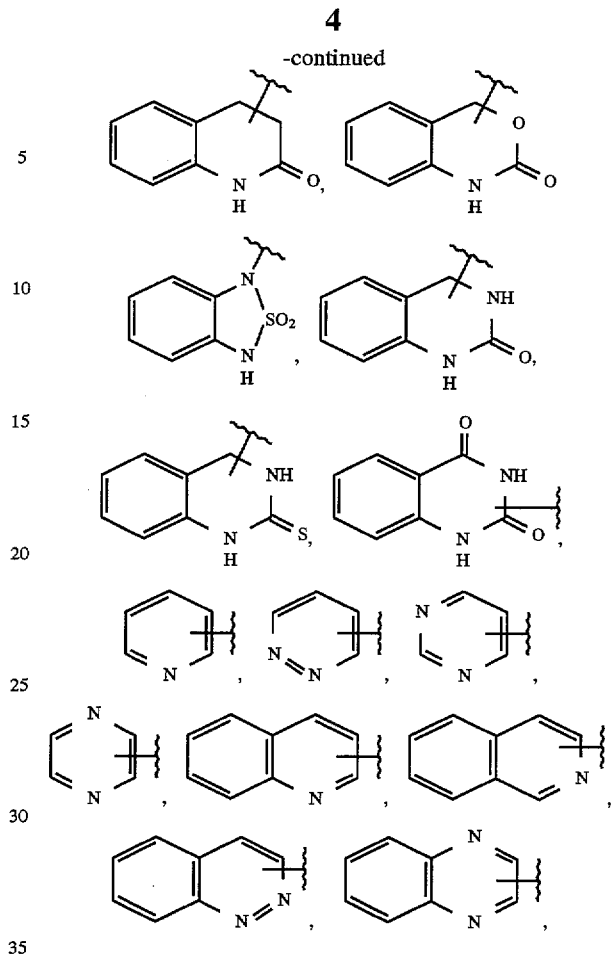

where the aryl is attached to the piperidine ring at an available carbon or nitrogen atom of the aryl, and where the aryl is optionally substituted on at least one available carbon or nitrogen atom by —$R^8$, wherein $R^8$ is independently selected from the group consisting of: hydrogen, $C_1$-$C_6$ alkyl, halogen, —$OR^6$, —$NHSO_2CF_3$, —$(CH_2)_rOR^6$, —$(CH_2)_rN(R^2)(R^6)$, —$(CH_2)_r(R^6)$, $CH_2)_rC(O)OR^6$—$(CH_2)_rOC(O)R^6$, —$(CH_2)_rC(O)R^6$, —$(CH_2)_rC(O)N(R^2)(R^2)$, —$(CH_2)_rC(O)N(R^2)(R^6)$, —$(CH_2)_rN(R^6)C(O)R^6$, —$(CH_2)_rN(R^6)C(O)OR^6$, —$(CH_2)_rN(R^2)C(O)N(R^2)(R^2)$, —$(CH_2)_rN(R^6)C(O)N(R^2)(R^6)$, —$(CH_2)_rN(R^6)SO_2R^6$, —$(CH_2)_rOC(O)N(R^2)(R^6)$, —$(CH_2)_rOC(O)N(R^2)(R^2)$, —$(CH_2)_rSO_2N(R^2)(R^6)$, —$(CH_2)_rSO_2N(R^2)(R^2)$, —$(CH_2)_rSO_2NHC(O)R^6$, —$(CH_2)_rSO_2NHC(O)OR^6$, —$(CH_2)_rC(O)NHC(O)N(R^2)(R^6)$, —$(CH_2)_rC(O)NHC(O)N(R^2)(R^2)$, —$(CH_2)_rC(O)NHC(O)R^6$, —$(CH_2)_rCONHSO_2R^6$, —$(CH_2)_rCONHSO_2N(R^2)(R^2)$, —$(CH_2)_rCONHSO_2N(R^2)(R^6)$, —$(CH_2)_rN(R^6)SO_2N(R^2)(R^2)$, —$(CH_2)_rN(R^6)SO_2N(R^2)(R^6)$, and —$(CH_2)_rS(O)_mR^6$;

$R^{3a}$ is selected from: hydrogen, and $C_1$-$C_6$ alkyl;

or $R^{3a}$ and one of X and Y may be joined to form a double bond;

or $R^3$ and $R^{3a}$ together may form a spiro system of the formula:

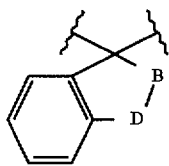

wherein B and D are independently selected from:
—C($R^2$)($R^8$)—, —C(O)—, —O—, —S(O)$_m$—, and —N$R^8$—, provided that if one of B or D is —O—, —S(O)$_m$—, and —N$R^8$—, then the other of B and D is not —O—, —S(O)$_m$—, or —N$R^8$—, wherein $R^8$ is as defined above with the option that if an $R^8$ group is present in both B and D such groups may be joined to form a double bond;

$R^4$ and $R^5$ are independently selected from:
hydrogen, $C_1$–$C_6$ alkyl, and substituted $C_1$–$C_6$ alkyl, wherein the substituents are selected from:
1 to 5 halo, 1 to 3 hydroxy, 1 to 3 $C_1$–$C_{10}$ alkanoyloxy, 1 to 3 $C_1$–$C_6$ alkoxy, phenyl, phenoxy, 2-furyl, $C_1$–$C_6$ alkoxycarbonyl, —S(O)$_m$($C_1$–$C_6$ alkyl); or $R^4$ and $R^5$ can be taken together to form —(CH$_2$)$_d$L$_a$(CH$_2$)$_e$— where L$_a$ is —C($R^2$)$_2$—, —O—, —S(O)$_m$— or —N($R^2$)—, d and e are independently 1 to 3 and $R^2$ is as defined above;

$R^6$ is hydrogen, $C_1$–$C_6$ alkyl, or (CH$_2$)$_v$aryl, wherein the alkyl and (CH$_2$)$_v$ groups may be optionally substituted by 1–2 —O($R^2$), —S(O)$_m$$R^2$, 1H-tetrazol-5-yl, —C(O)O$R^2$, —C(O)N($R^2$)($R^2$), —SO$_2$N($R^2$)($R^2$), or —N($R^2$)C(O)N($R^2$)($R^2$), and where aryl is selected from:
phenyl, naphthyl, pyridyl, 1H-tetrazol-5-yl, triazolyl, imidazolyl, indolyl, thiazolyl, pyrazolyl, thiadiazolyl, imidazolone-1-yl, oxadiazolyl, benzimidazol-2-yl, triazolinone-yl, quinolinyl, isoquinolinyl, and wherein the aryl is optionally substituted with 1 to 2 halogen, 1 to 2 —$R^2$, —O$R^2$, or —N($R^2$)($R^2$);

A is:

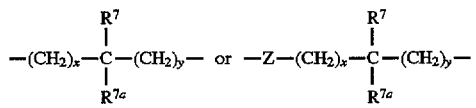

where x and y are independently 0, 1, 2 or 3;
Z is N—$R^{6a}$ or O, where $R^{6a}$ is hydrogen or $C_1$–$C_6$ alkyl;
$R^7$ and $R^{7a}$ are independently selected from:
hydrogen, $C_1$–$C_6$ alkyl, trifluoromethyl, phenyl, and substituted $C_1$–$C_6$ alkyl where the substituent is selected from: imidazolyl, phenyl, naphthyl, indolyl, p-hydroxyphenyl, —O$R^2$, —S(O)$_m$$R^2$, —C(O)O$R^2$, $C_3$–$C_7$ cycloalkyl, —N($R^2$)($R^2$), and —C(O)N($R^2$)($R^2$), or $R^7$ and $R^{7a}$ may independently be joined to one or both of $R^4$ and $R^5$, groups to form alkylene bridges between the terminal nitrogen and the alkyl portion of the $R^7$ or $R^{7a}$ groups, wherein the bridge contains 1 to 5 carbons atoms, or $R^7$ and $R^{7a}$ can be joined to one another to form a $C_3$–$C_7$ cycloalkyl;

X is selected from the group consisting of:
hydrogen, —C≡N, —(CH$_2$)$_q$N($R^6$)C(O)$R^6$, —(CH$_2$)$_q$N($R^6$)SO$_2$$R^6$, —(CH$_2$)$_q$N($R^6$)C(O)N($R^2$)($R^6$)—(CH$_2$)$_q$C(O)N($R^2$)($R^2$), —(CH$_2$)$_q$C(O)N($R^2$)($R^6$)—(CH$_2$)$_q$C(O)O$R^6$, —(CH$_2$)$_q$O$R^6$, —(CH$_2$)$_q$OC(O)$R^6$, —(CH$_2$)$_q$OC(O)N($R^2$)($R^6$)—(CH$_2$)$_q$OC(O)N($R^2$) ($R^2$), —(CH$_2$)$_q$C(O)$R^6$, —(CH$_2$)$_q$N($R^6$)C(O)O$R^6$, (CH$_2$)$_q$N($R^6$)SO$_2$N($R^2$)($R^6$), (CH$_2$)$_q$N($R^6$)SO$_2$N($R^2$) ($R^2$) and —(CH$_2$)$_q$S(O)$_m$$R^6$, where an $R^2$, and the (CH$_2$)$_q$ and group may be optionally substituted by 1 to 2 $C_1$–$C_4$ alkyl, hydroxyl, $C_1$–$C_4$ lower alkoxy, carboxyl, —CONH$_2$, —S(O)$_m$CH$_3$, carboxylate $C_1$–$C_4$ alkyl ester, or 1H-tetrazol-5-yl, and where aryl is selected from: phenyl, naphthyl, quinolinyl, isoquinolinyl, pyridyl, thiazolyl, and 1H-tetrazol-5-yl, and where the aryl is optionally substituted by 1 to 3 halogen, 1 to 3 —O$R^2$, —CON($R^2$)($R^2$), —C(O)O$R^2$, 1 to 3 $C_1$–$C_4$ alkyl, —S(O)$_m$$R^2$, or 1H-tetrazol-5-yl;

Y is selected from the group consisting of:
hydrogen, $C_1$–$C_{10}$ alkyl, —(CH$_2$)$_q$aryl, —(CH$_2$)$_q$($C_3$–$C_7$ cycloalkyl), —(CH$_2$)$_q$—K—($C_1$–$C_6$ alkyl), —(CH$_2$)$_q$—K—(CH$_2$)$_r$aryl, —(CH$_2$)$_q$—K—(CH$_2$)$_t$($C_3$–$C_7$ cycloalkyl where K is O, S(O)$_m$, C(O)N$R^2$, CH=CH, C≡C, N($R^2$)C(O), C(O)N$R^2$, C(O)O, or OC(O), and where the alkyl, $R^2$, (CH$_2$)$_q$ and (CH$_2$)$_r$ groups are optionally substituted by $C_1$–$C_4$ alkyl, hydroxyl, $C_1$–$C_4$ lower alkoxy, carboxyl, —CONH$_2$ or carboxylate $C_1$–$C_4$ alkyl esters, and where aryl is selected from: phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrrazinyl, and isothiazolyl, and where the aryl is optionally substituted by 1 to 3 halogen, 1 to 3 —O$R^2$, —C(O)O$R^2$, —C(O)N($R^2$)($R^2$), nitro, cyano, benzyl, 1 to 3 $C_1$–$C_4$ alkyl, —S(O)$_m$$R^2$, or 1H-tetrazol-5-yl;

m is 0, 1, or 2;
q is 0, 1, 2, 3, or 4;
r is 0, 1, 2, or 3;
t is 0, 1, 2, or 3;
v is 0, 1, or 2;
and pharmaceutically acceptable salts and individual diastereomers thereof.

In the above structural formula and throughout the instant specification, the following terms have the indicated meanings:

The alkyl groups specified above are intended to include those alkyl groups of the designated length in either a straight or branched configuration which may optionally contain double or triple bonds. Exemplary of such alkyl groups are methyl (Me), ethyl (Et), propyl (Pr), isopropyl (i-Pr), butyl (Bu), sec-butyl (s-Bu), tertiary butyl (t-Bu), pentyl, isopentyl, hexyl, isohexyl, allyl, propinyl, butadienyl, hexenyl and the like.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, propinyloxy, isobutenyloxy, hexenyloxy and the like.

The term "halogen" is intended to include the halogen atom fluorine, chlorine, bromine and iodine.

The term "aryl" within the present invention, unless otherwise specified, is intended to include aromatic rings, such as carbocyclic and heterocyclic aromatic rings selected the group consisting of: phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrrazinyl, or isothiazolyl, which may be optionally substituted by 1 to 3 of $C_1$–$C_6$ alkyl, 1 to 3 of halogen, 1 to 2 of —$OR^2$, methylenedioxy, —$S(O)_m R^2$, 1 to 2 of —$CF_3$, —$OCF_3$, nitro, —$N(R^2)C(O)(R^2)$, —$C(O)OR^2$, —$C(O)N(R^2)(R^2)$, -1H-tetrazol-5-yl, —$SO_2N(R^2)(R^2)$, —$N(R^2)SO_2$ phenyl, or —$N(R^2)SO_2R^2$, wherein $R^2$ is as defined herein.

Certain of the above defined terms may occur more than once in the above formula or definitions and upon such occurrence, each term shall be defined independently of the other.

Preferred compounds of the instant invention include those of Formula Ia:

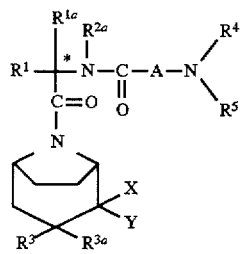

Formula Ia wherein:

$R^1$ is selected from the group consisting of:
$C_1$–$C_{10}$ alkyl, aryl ($C_1$–$C_4$ alkyl)-, $C_3$—$C_6$ cycloalkyl ($C_1$–$C_4$ alkyl)-, ($C_1$–$C_4$ alkyl)-K—($C_1$–$C_2$ alkyl)-, aryl ($C_0$–$C_2$ alkyl)-K-($C_1$–$C_2$ alkyl)-, and ($C_3$–$C_7$ cycloalkyl)($C_0$–$C_2$ alkyl)-K—($C_1$–$C_2$ alkyl)-, where K is —O—, —$S(O)_m$—, —OC(O)—, —C(O)O— and the alkyl groups may be further substituted by 1 to 7 halogen, $S(O)_m R_2$, 1 to 3 $OR_2$ or $C(O)OR_2$ and aryl is phenyl, naphthyl, indolyl, pyridyl, benzothienyl, or benzofuranyl which may be further substituted by 1-2 $C_1$–$C_4$ alkyl, 1 to 2 halogen, 1 to 2 —$OR^2$, —$S(O)_m R_2$, or —$C(O)OR_2$;

$R^{1a}$ is hydrogen, or $C_1$–$C_6$ alkyl;

$R^2$ is selected from the group consisting of:
hydrogen, $C_1$–$C_6$ alkyl, and $C_3$–$C_7$ cycloalkyl and where two $C_1$–$C_6$ alkyl groups are present on one atom they may be optionally joined to form a $C_4$–$C_7$ cyclic ring optionally including oxygen, sulfur or $NR_{3a}$;

$R^{2a}$ is hydrogen, or $C_1$–$C_6$ alkyl;

$R^3$ is hydrogen or phenyl optionally substituted in the ortho position by a $C_1$–$C_6$ alkyl group, —$NHSO_2CF_3$, —$(CH_2)_r(1H$-tetrazol-5-yl), —$(CH_2)_rC(O)OR_2$, or —$(CH_2)_rC(O)N(R_2)(R_6)$;

$R^{3a}$ is hydrogen, or $C_1$–$C_4$ alkyl;

or $R^3$ and $R^{3a}$ together may form a spiro system of the formula:

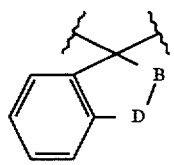

wherein B and D are independently selected from:
—$C(R^2)(R^8)$—, —C(O)—, —O—, —$S(O)_m$—, and —$NR^8$—, provided that if one of B or D is —O—, —$S(O)_m$—, and —$NR^8$—, then the other of B and D is not —O—, —$S(O)_m$—, or —$NR^8$—, $R^4$ and $R^5$ are independently hydrogen, $C_1$–$C_6$ alkyl, or substituted $C_1$–$C_6$ alkyl where the substituents are selected from: 1 to 5 halo, 1 to 3 hydroxyl, —$S(O)_m$ ($C_1$–$C_6$ alkyl), and phenyl;

$R^6$ is hydrogen, $C_1$–$C_6$ alkyl, or $(CH_2)_v$aryl, wherein the alkyl and $(CH_2)_v$ groups may be optionally substituted by 1-2 —$O(R^2)$, —$S(O)_m R^2$, 1H-tetrazol-5-yl, —$C(O)OR^2$, —$C(O)N(R^2)(R^2)$, —$SO_2N(R^2)(R^2)$, or —$N(R^2)C(O)N(R^2)(R^2)$, and where aryl is selected from: phenyl, naphthyl, quinolinyl, pyridyl, 1H-tetrazol-5-yl, triazolyl, imidazolyl, thiazolyl, pyrazolyl, thiadiazolyl, imidazolone- 1-yl, oxadiazolyl, benzimidazol-2-yl, triazolinone-yl, and wherein the aryl is optionally substituted with 1 or 2 halogen, —$R^2$, —$OR^2$ or —$NR^2R^2$;

A is:

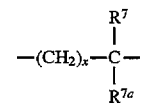

where x is 0, or 1;

$R^7$ and $R^{7a}$ are independently hydrogen $C_1$–$C_6$ alkyl, trifluoromethyl, phenyl, substituted $C_1$–$C_6$ alkyl where the substituents are imidazolyl, phenyl, indolyl, p-hydroxyphenyl, —$OR^2$, —$S(O)_m R^2$, —$C(O)OR^2$, $C_5$–$C_7$ cycloalkyl, —$N(R^2)(R^2)$, —$C(O)N(R^2)(R^2)$; or $R^7$ and $R^{7a}$ can independently be joined to one of $R^4$ or $R^5$ to form alkylene bridges between the terminal nitrogen and the alkyl portion of $R^7$ or $R^{7a}$ groups to form 5 or 6 membered rings; or $R^7$ and $R^{7a}$ can be joined to one another to form a $C_3$ cycloalkyl;

$R^8$ is independently selected from the group consisting of:
hydrogen, $C_1$–$C_6$ alkyl, —$(CH_2)_rOR^6$, —$(CH_2)_2C(O)OR^6$, —$(CH_2)_rC(O)N(R^2)(R^6)$, —$(CH_2)_rC(O)N(R^2)R^2)$, —$(CH_2)_rN(R^2)C(O)R^6$, —$(CH_2)_rN(R^2)C(O)N(R^2)(R^6)$, —$(CH_2)_rN(R^2)C(O)N(R^2)R^6)$, —$(CH_2)_rR^6$, —$(CH_2)_rS(O)_m R^6$, —$(CH_2)_rSO_2N(R^2)(R^6)$, —$(CH_2)_rSO_2N(R^2)(R^2)$, and —$(CH_2)_rN(R^2)SO_2N(R^2)(R^6)$;

X is selected from the group consisting of: hydrogen, —$(CH_2)_qC(O)N(R^2)(R^6)$, —$(CH_2)_qC(O)OR^6$, —$(CH_2)_qN(R^6)C(O)R^6$, and —$(CH_2)_qN(R^6)SO_2R^6$;

Y is selected from the group consisting of: hydrogen, $C_1$–$C_8$ alkyl, —$(CH_2)_t$ phenyl, —$(CH_2)_t$ pyridyl, and —$(CH_2)_t$thiazolyl;

m is 0, 1, or 2;

q is 0 or 1;

r is 0, 1, 2, or 3;

t is 0 or 1;

v is 0, 1, or 2;

and pharmaceutically acceptable salts and individual diastereomers thereof.

The most preferred compounds of the present invention include the following:

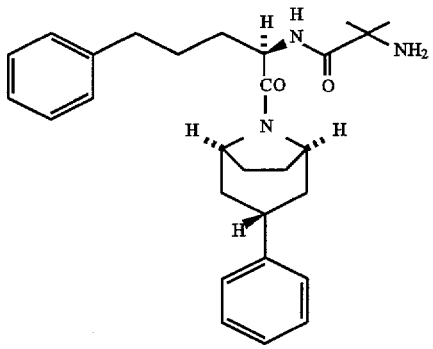
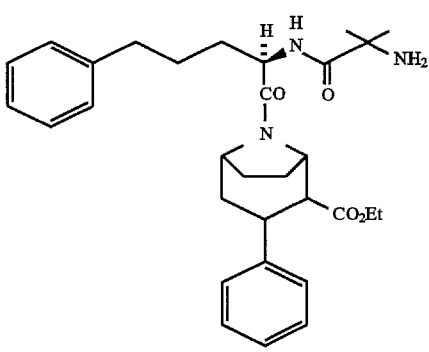
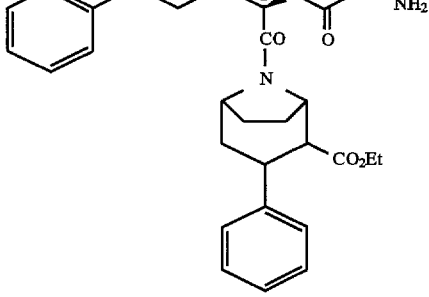
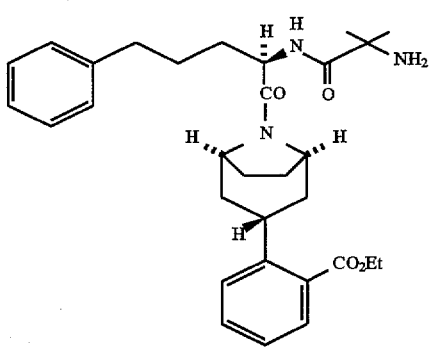
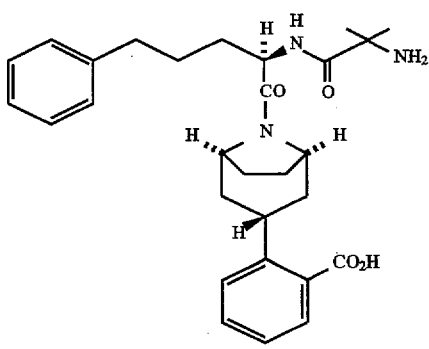

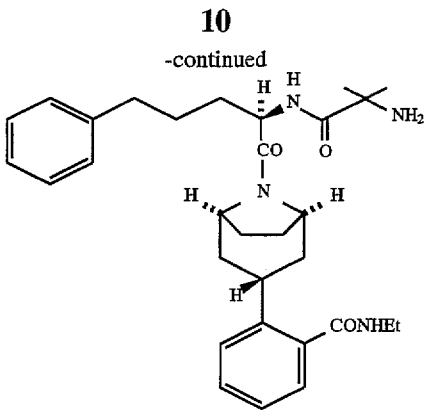
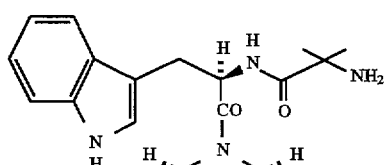
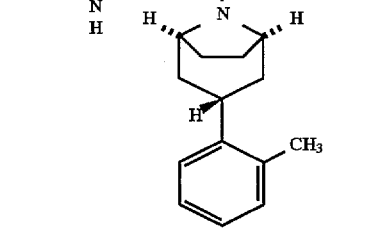

and their pharmaceutically acceptable salts and individual diasteromers thereof, where not otherwise specified.

All of the most preferred compounds shown above have an asymmetric center, which is shown in its preferred (R)-stereochemistry.

Throughout the instant application, the following abbreviations are used with the following meanings:

| | | |
|---|---|---|
| BOC | t-butyloxycarbonyl | |
| BOP | Benzotriazol-1-yloxy tris(dimethylamino)-phosphonium hexafluorophosphate | |
| CBZ | Benzyloxycarbonyl | |
| DIBAL-H | diisobutylaluminum hydride | |
| DMF | N,N-dimethylformamide | |
| EDC | 1-(3-dimethylaminopropyl)-3-ethylcarbodiimide hydrochloride | |
| FAB-MS | Fast atom bombardment-mass spectroscopy | |
| GHRP | Growth hormone releasing peptide | |
| HOBT | Hydroxybenztriazole | |
| LAH | Lithium aluminum hydride | |
| HPLC | High pressure liquid chromatography | |
| MHz | Megahertz | |
| MPLC | Medium pressure liquid chromatography | |
| NMM | N-Methylmorpholine | |
| NMR | Nuclear Magnetic Resonance | |

| | |
|---|---|
| PLC | Preparative liquid chromatography |
| RPLC | Reverse phase liquid chromatography |
| TFA | Trifluoroacetic acid |
| THF | Tetrahydrofuran |
| TLC | Thin layer chromatography |
| TMS | Tetramethylsilane |

The compounds of the instant invention all have at least one asymmetric center as noted by the asterisk in the structural Formula I:

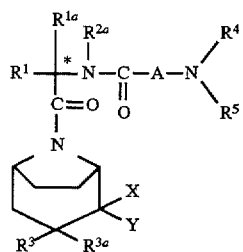

Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the ambit of the instant invention. In addition $R^3$, $R^{3a}$, X and Y may be in either a cis- or trans- relationship to the ethano bridging group and both of these arrangements are within the scope of this invention. When $R^3$ is aryl or substituted aryl, its preferred orientation is trans- to the ethano bridge. Compounds which are more active as growth hormone secretagogues and, therefore are preferred, are those in which the nitrogen substituent on the carbon bearing $R^1$ is above and the hydrogen atom is below the plane of the structure as represented in Formula II. An equivalent representation places $R^1$ and the N-substituent in the plane of the structure with the C=O group above the plane of the structure.

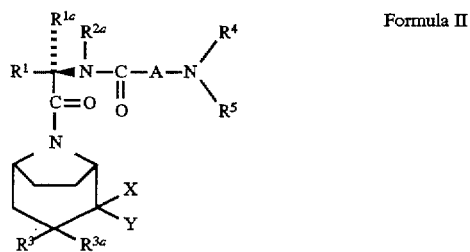

Formula II

This configuration corresponds to that present in a D-amino acid. In most cases, this is also designated as an R-configuration although this will vary according to the value of $R^1$ used in making the R- or S- stereochemical assignments. Their absolute stereochemistry may be determined by the X-ray crystallography of crystalline products or crystalline intermediates which are derivatized, if necessary, containing an asymmetric center of known configuration.

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The preparation of compounds of Formula I of the present invention can be carried out in sequential or convergent synthetic routes. Syntheses detailing the preparation of the compounds of Formula I in a sequential manner are presented in the following reaction schemes.

The phrase "standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The uses of protective groups for amine and carboxylic acid to facilitate the desired reaction and minimize undesired reactions are well documented. Conditions required to remove protecting groups which may be present are found in Greene, T; Wuts, P. G. M. *Protective Groups in Organic Synthesis*, John Wiley & Sons, Inc., New York, N.Y. (1991). CBZ and BOC were used extensively in the syntheses of this invention, and their removal conditions are known to those skilled in the art. Removal of CBZ groups can be achieved by a number of methods, for example, catalytic hydrogenation with hydrogen in the presence of palladium catalyst in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethylsulfide. Removal of BOC protecting groups is carried out in a solvent such as methylene chloride or methanol, with a strong acid, such as trifluoroacetic acid (TFA) or hydrochloric acid (HCl).

The protected amino acid derivatives 1 are, in many cases, commercially available, where the protecting group L is, for example, BOC or CBZ groups. Other protected amino acid derivatives 1 can be prepared by literature methods (Williams, R. M. *Synthesis of Optically Active α-Amino Acids*, Pergamon Press: Oxford, 1989). Many of the piperidines of Formula 2 are either commercially available or known in the literature and others can be prepared following literature methods, some of which are described here. The skills required in carrying out the reaction and purification of the resulting reaction products are known to those skilled in the art. Purification procedures include crystallization, normal phase or reverse phase chromatography.

SCHEME 1

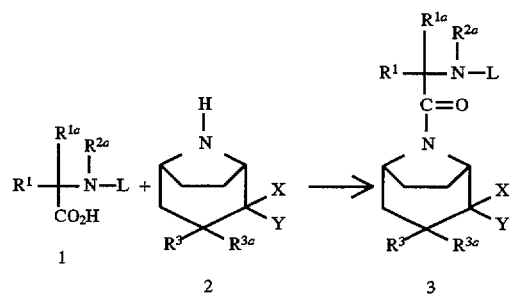

Intermediates of Formula 3 can be synthesized as described in Scheme 1. Coupling of amine of Formula 2, whose preparations are described later if they are not commercially available, to protected amino acids of Formula 1, wherein L is a suitable protecting group, is conveniently carried out under standard peptide coupling conditions.

SCHEME 2

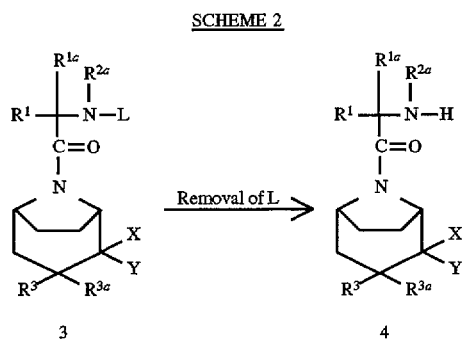

Conversion of 3 to intermediates 4 can be carried out as illustrated in Scheme 2 by removal of the protecting group L (CBZ, BOC, etc.)

SCHEME 3

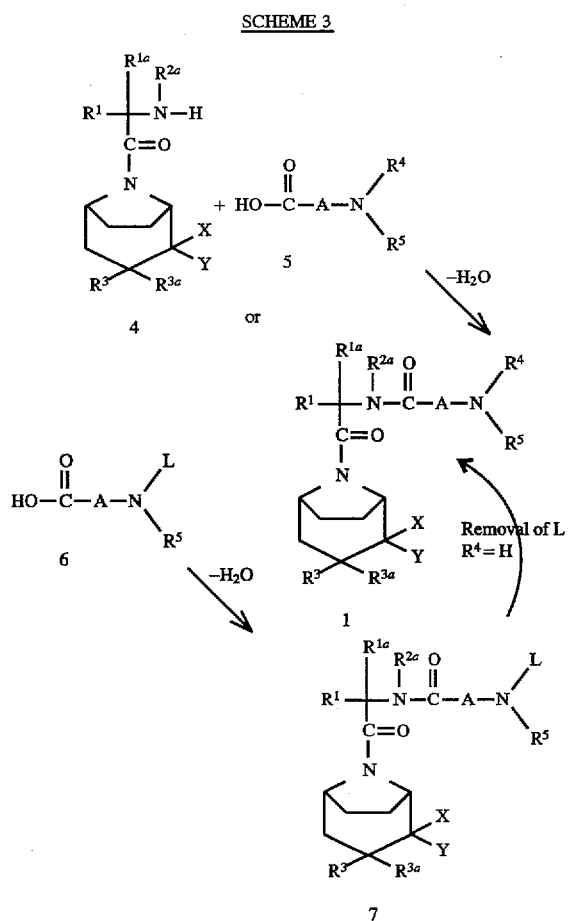

Intermediates of Formula 5, wherein A is connected to the carbonyl by a carbon atom —$(CH_2)_x CR^7 R^{7a}(CH_2)_y$— as shown in Scheme 3 can be coupled to intermediates of formula 4 under the standard peptide coupling reaction conditions. The amino acids 5, as amino acids 1, are either commercially available or may be synthesized. Also if $R^4$ or $R^5$ is a hydrogen then the protected amino acids 6 are employed in the coupling reaction, wherein L is a protecting group as defined above. Removal of L in 7 to afford I, where $R^4$=H, can be carried out under conditions known in the art.

SCHEME 4

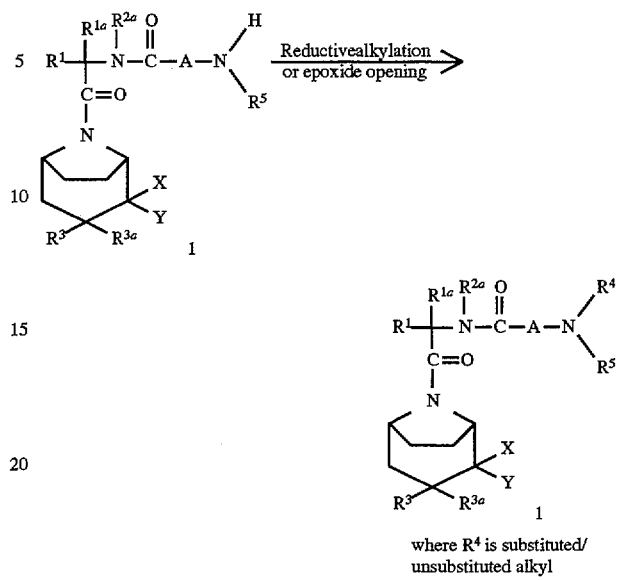

where $R^4$ is substituted/unsubstituted alkyl

Compounds of Formula I wherein $R^4$ and/or $R^5$ is a hydrogen can be further elaborated to new compounds I (for example, with side chains $R^4$=$CH_2$—CH(OH)—$CH_2X$, wherein X=H or OH) which are substituted on the amino group as depicted in Scheme 4. Reductive alkylation of I with an aldehyde is carried out under conditions known in the art; for example, by catalytic hydrogenation with hydrogen in the presence of platinum, palladium, or nickel catalysts or with chemical reducing agents such as sodium cyanoborohydride in a protic solvent such as methanol or ethanol in the present of catalytic amount of acid. Alternatively, a similar transformation can be accomplished via an epoxide opening reaction.

SCHEME 5

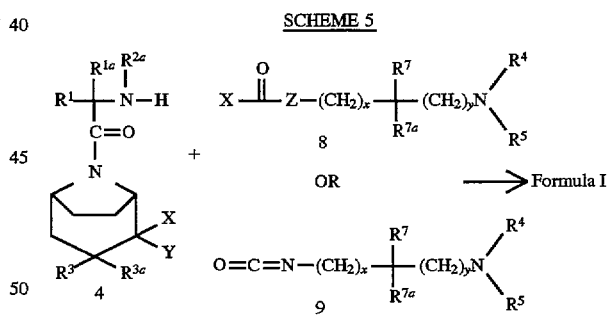

Compounds of Formula I, wherein A is Z—$(CH_2)_x$—C$(R^7)(R^{7a})$—$(CH_2)_y$ and Z is N—$R^2$ or O can be prepared as shown in Scheme 5 by reacting 4 with reagent 8, wherein X is an appropriate leaving group such as Cl, Br, I, or imidazole. Alternatively, 4 can be reacted with an isocyanate of formula 9 in an inert solvent such as 1,2-dichloroethane which results in a compound of Formula I where Z is NH.

The compounds of general Formula I of the present invention can also be prepared in a convergent manner as described in reaction schemes 6, 7 and 8.

The carboxylic acid protected amino acid derivatives 10 are, in many cases, commercially available where M=methyl, ethyl, or benzyl esters. Other ester protected amino acids can be prepared by classical methods familiar to those skilled in the art. Some of these methods include the reaction of the amino acid with an alcohol in the presence of an acid such as hydrochloric acid or p-toluenesulfonic acid and azeotropic removal of water. Other methods includes the reaction of a protected amino acid with a diazoalkane and removal of the protecting group L.

mation of 7 to I is achieved by removal of the protecting group L. When $R^4$ and/or $R^5$ is H, substituted alkyl groups may be optionally added to the nitrogen atom as described in Scheme 4.

SCHEME 6

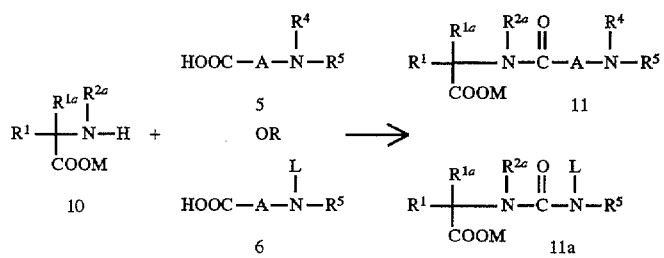

Intermediates of Formula 11 or 11a, can be prepared as shown in Scheme 6 by coupling of amino acid esters 10 to amino acids of Formula 5 or 6. When a urea linkage is present in 11 or 11a, it can be introduced as illustrated in Scheme 5.

SCHEME 7

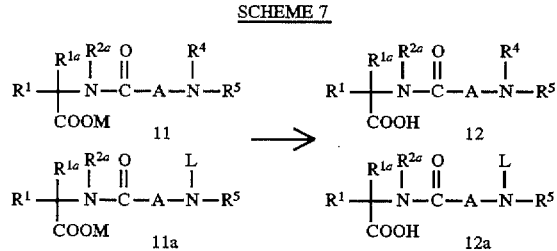

Conversion of the ester 11 or 11a to intermediate acids 12 or 12a can be achieved by a number of methods known in the art as described in Scheme 7. For example, methyl and ethyl esters can be hydrolyzed with lithium hydroxide in a protic solvent like aqueous methanol. In addition, removal of benzyl group can be accomplished by a number of reductive methods including hydrogenation in the presence of palladium catalyst in a protic solvent such as methanol. An allyl ester can be cleaved with tetrakis-triphenylphosphine palladium catalyst in the presence of 2-ethylhexanoic acid in a variety of solvents including ethyl acetate and dichloromethane (see *J. Org. Chem.*, 42, 587 (1982)).

SCHEME 8

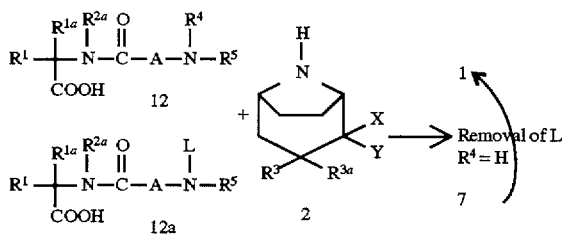

Acid 12 or 12a can then be elaborated to I or compound 7 as described in Scheme 8. Coupling of bridged piperidines of formula 2 to acids of Formula 12 or 12a, wherein L is a suitable protecting group, is conveniently carried out under the standard peptide coupling reaction conditions. Transfor- The substituted bridged piperidines are either known compounds or can be prepared by literature procedures. Illustrated here are some, but by no means all the methods available for their preparation.

Bridged piperidines of Formula 13 including those shown in Table 1 are known and constitute useful intermediates for the preparation of compounds of the present invention. In addition, various 3-carboxylate ester derivatives of these ketones (e.g. compound 15 wherein $R^3$ and $R^{3a}$ are ketone, X is $CO_2R^6$, and Y is hydrogen) including those of Table 1 have been described in the art. These compounds also may be employed as synthetic intermediates for the preparation of the compounds of the present invention.

TABLE 1

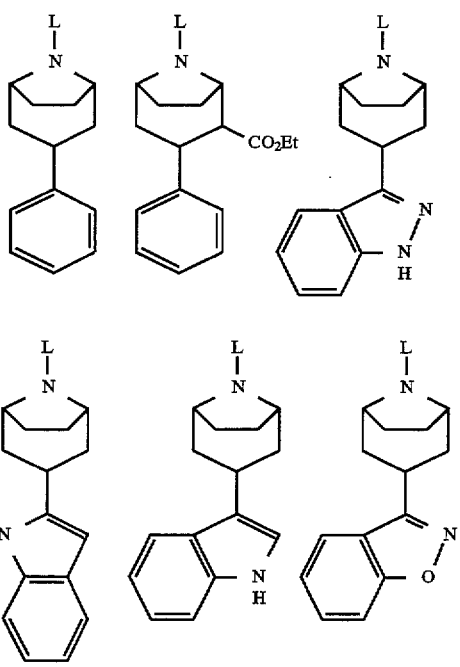

TABLE 1 -continued

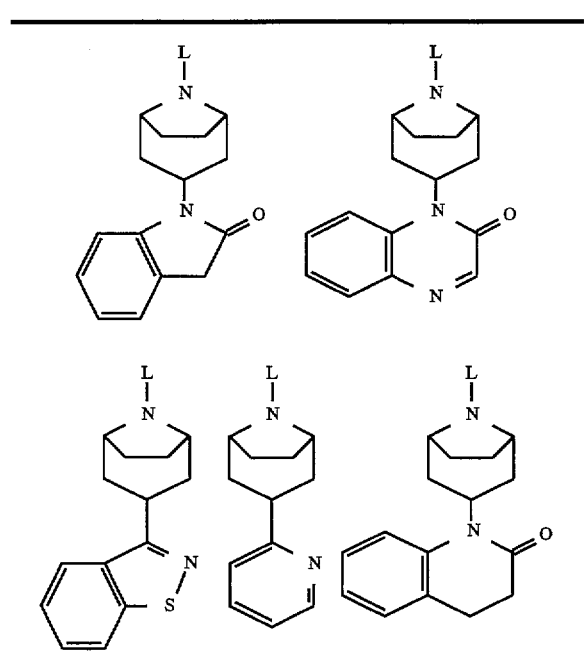

SCHEME 9

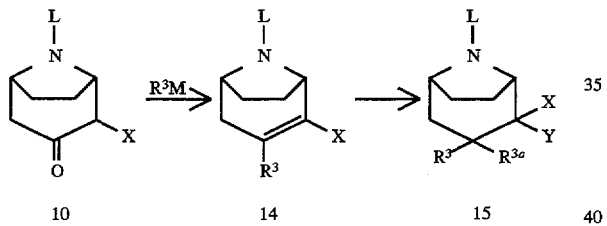

As shown in Scheme 9, a general method that may be utilized to prepare a variety of 4-substituted bridged piperidines of formula 2 involves the addition of a metalated aryl (for e.g., phenyls, naphthyls, pyridines, thiophenes, benzothiophenes, quinolines, indoles) to a protected 4-piperidone of Formula 13 (L is a methyl or benzyl group) to give a 4-hydroxy compound that can dehydrated to give bridged tetrahydropyridines of Formula 14 by methods familiar to those skilled in the art. Removal of L from bridged piperidines of formula 14 may be carried out by a number of methods, including the cyanogen bromide protocol detailed by H. Ong et at., in *J. Med. Chem.*, 23, 981–986 (1983) and the ACE-Cl method as described in R. Olofson et al., *J. Org. Chem.*, 23, 2795 (1984). The 4-substituted bridged tetrahydropiperidines obtained by this method can be elaborated to the instant compounds by utilizing chemistry detailed in Schemes 1–8. The bridged piperidines of Formula 14 can be hydrogenated by use of platinum or palladium catalysts in a protic solvent like methanol or alkylated to give piperidines of Formula 15 which can also be elaborated to the instant compounds of Formula I.

SCHEME 10

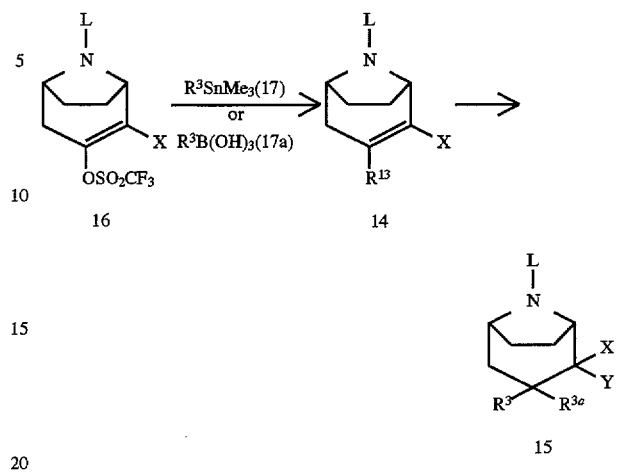

As shown in Scheme 10, other methods may also be utilized to synthesize bridged piperidines of Formula 2. For example, cross-coupling of enol triflates of Formula 16 (L=protecting group) with heteroarylboronic acids of Formula 17a or heteroaryl tin reagents of formula 17, wherein $R^3$ may be any of a number of the aryls presented herein, may be accomplished with palladium (II) or palladium (0) catalysts as detailed in the review article by W. J. Scott and J. E. McMurry, *Acc. Chem. Res.*, 21, 47 (1988) to give tetrahydropiperidines 14 (L=protecting group). Various methods exist for the synthesis of the enol triflate intermediates of Formula 16, aryl boronic acids 17a and aryl tin reagents of Formula 17 and can be prepared by methods that are familiar to those skilled in the art. Removal of the protecting group L furnishes piperidines of Formula 14 (L=H). Hydrogenation of 14 followed by removal of the protection group L gives saturated derivatives 15 (L=H).

SCHEME 10A

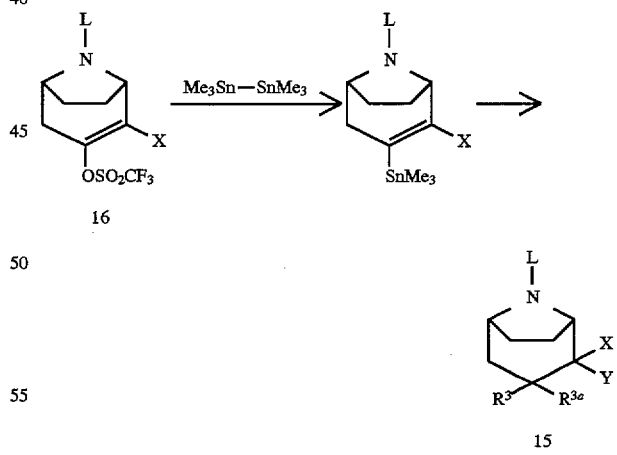

Alternatively, as shown in Scheme 10A, the vinyl triflate 16 may be convened to the corresponding vinyl tin reagent by treatment with hexamethylditin in the presence of a palladium catalyst. The vinyl tin compound is then coupled with an appropriate aryl halide or aryl triflate as described above to give the compound 15. Removal of the protecting group provides intermediate 15 (L=H), which is elaborated to the instant compounds via the procedures described in Schemes 1–8.

SCHEME 10B

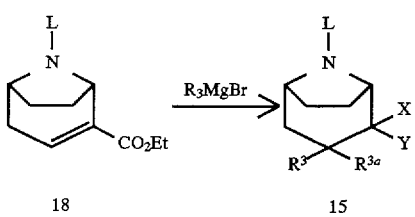

In addition, as shown in Scheme 10B, bridged piperidines of the formula 15 (wherein $R^3$ is aryl, X is CO2Et, and Y is hydrogen) may be prepared essentially as described by R. L. Clarke, et al., *J. Med. Chem.*, 16, 1260–1267 (1973). In this method, an aryl grignard reagent is added to an unsaturated ester such as compound 18 to give the compound 15. Removal of the protecting group provides intermediates 15 (L═H), which is elaborated to the instant compounds via the procedures described in Schemes 1–8.

SCHEME 11

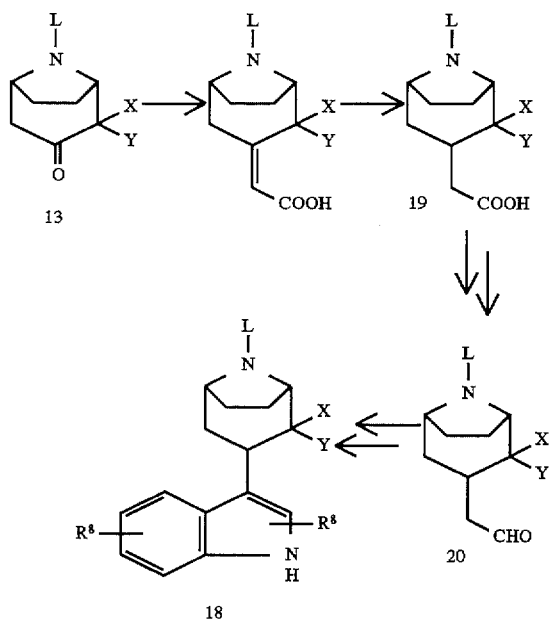

Bridged piperidines of Formula 18, wherein $R^8$ may be any of the substituents as described herein, may be prepared from the protected bridged piperidine acetic acid compound 19 (L═CBZ) as shown in Scheme 11. The acid 19 is readily available by Wittig olefination of the ketone 13 followed by reduction of the olefin and base hydrolysis of the ester. Treatment of 19 with either oxalyl chloride or thionyl chloride in an inert solvent like benzene or carbon tetrachloride gives the corresponding acid chloride that is converted to the aldehyde 20 by a Rosemund reduction. Compound 20 is then elaborated to a variety of substituted indoles 18 by utilizing the Fischer indole synthesis (see *J. Chem. Soc. Chem. Commun.*, 563 (1981); *J. Chem. Soc.*, 3175 (1957)). The protecting group L (for e.g., CBZ) can be removed by standard protocols and elaborated to the instant compounds by using chemistry presented in Schemes 1–8.

SCHEME 12

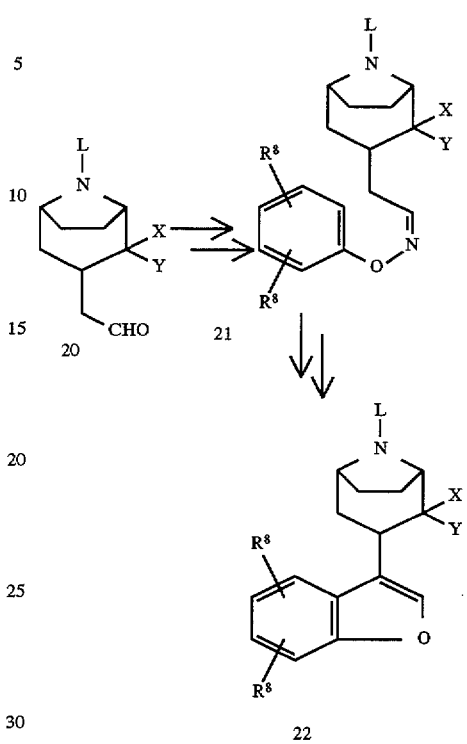

An analogous synthesis of benzofurans of Formula 22 from o-aryloximes is exemplified by the transformation of 21 to 22 (see *Tetrahedron Lett.*, 2867 (1967)) as depicted in Scheme 12.

SCHEME 13

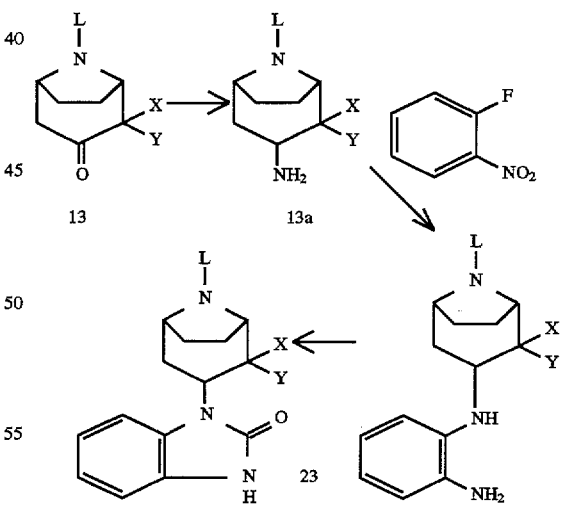

The bridged 4-(2-keto-1-benzimidazolinyl)piperidine compound 23 may be prepared as shown in Scheme 13. Treatment of the ketone 13 with hydroxylamine hydrochloride followed by hydrogenation of the resulting oxime gives the amine 13a. The amine is then reacted with o-nitrofluorobenzene to give the aniline, followed by reduction and cyclization with carbonyldiimidazole to give 23.

SCHEME 13A

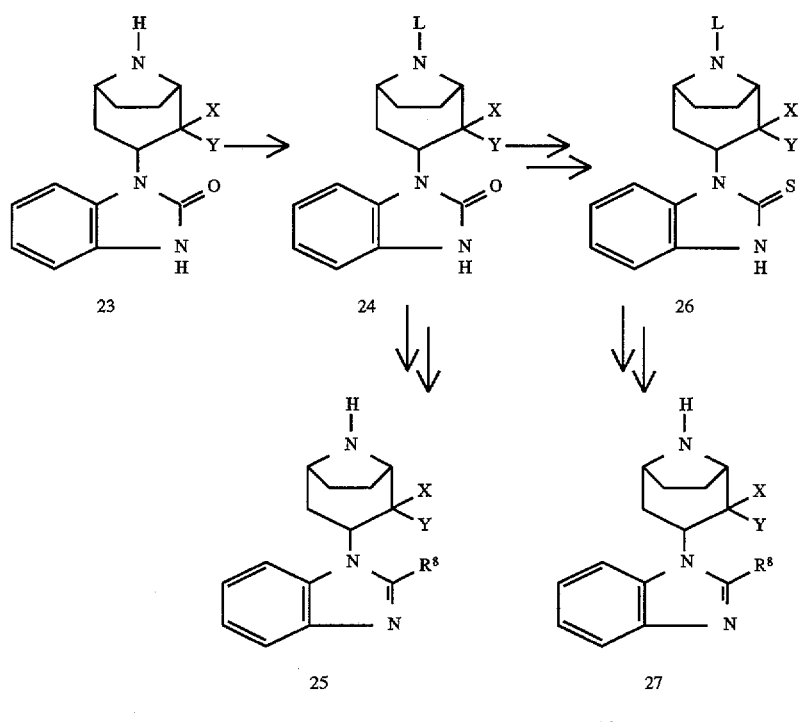

The bridged 4-(2-keto-1-benzimidazolinyl)piperidine compound 23 may be elaborated to the instant compounds by using chemistry detailed in Schemes 1–8. Furthermore, 23 can serve as an intermediate for the synthesis of instant compounds bearing other aryl substituents as shown in Scheme 13A. Protection of the piperidine with a protecting group L (for e.g., BOC or CBZ) to give 24 can be carried out by methods familiar to those skilled in the art. The bridged piperidine 24 can be treated with a base in an inert solvent like dry tetrahydrofuran or dimethylformamide and the anion can be trapped with electrophiles like alkyl halides and acyl chlorides to give benzimidazoles of Formula 25. As shown in Scheme 13, 24 can be treated with Lawesson's reagent in an inert solvent such as toluene to give the piperidine of Formula 26 which can be transformed to the instant compounds after removal of the protecting group L. The compound 26 can be elaborated further to provide compounds of Formula 27 by treatment of it with base followed by trapping of the thiolate anion thereby generated with alkyl halides.

SCHEME 14

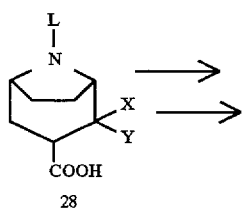

-continued
SCHEME 14

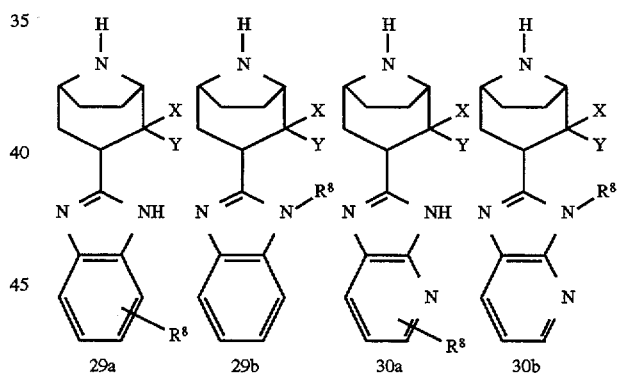

As shown in Scheme 14, other heterocyclic piperidines of Formula 2 may be synthesized from a 4-carboxyl piperidine of Formula 28 wherein L is a methyl or benzyl group. Compound 28 is reacted with ortho-phenylenediamines or ortho-diamino pyridines in a solvent such as polyphosphoric acid to give benzimidazoles of Formula 29a and 29b, and imidazopyridines of Formula 30a and 30b. As noted previously, 29a, 29b, 30a and 30b may be elaborated to the instant compounds following removal of the protecting group L.

SCHEME 14A

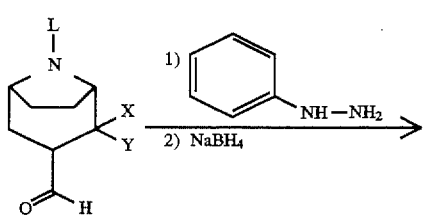

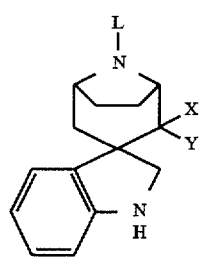

As shown in Scheme 14A, bridged piperidines bearing a 4,4-spiro substituent may be prepared from a piperidine 4-carboxaldehyde and a phenylhydrazone via a Fisher indole synthesis. The amine of the spiro intermediate may be further alkylated, acylated, or sulfonylated to obtain additional intermediates. Removal of the protecting group L and the procedures of Schemes 1–8 allow for preparation of the desired compounds of the present invention.

In addition, acids, acid chlorides, nitriles, and iminoethers at the 4-position of the a protected piperidine may serve as key intermediates in the preparation of a number of alkyl, phenyl, hydroxy, and amino-substituted heterocycles. Many of the methods are documented in A. Katrizky, *Handbook of Heterocycles* Pergamon Press, New York, N.Y. (1985) and may be used to synthesize the instant compounds bearing a variety of heterocycles.

The substituent on the 4-position of the piperidine ring may be either cis- or trans- to the ethano bridge. These isomers may be separated by numerous methods including chromatography or crystallization. Determination of the cis- or trans- stereochemistry in a given compound is best established by x-ray crystallography of a crystalline intermediate or a final product. With respect to 3,4-disubstituted compound, NMR spectra are useful to establish the relative cis- or trans- orientation. If the 3-position is substituted, an additional cis- or trans- relationship will be present. Enantiomers may be resolved at the stage of the piperidine intermediate by numerous methods, including the classical resolution of racemates. For example resolution can be achieved by the formation of diastereomeric salts of racemic amines with optically active acids such as D- and L- tartaric acid or (±)-camphorsulfonic acid. Furthermore, diastereomeric compounds are produced if the amino acid bearing the $R^1$ substituent is optically active and is attached to a bridged piperidine bearing a substituent at the 3-position. Such diastereomers may be separated as intermediates or final products by various methods such as chromatography.

The compounds of the present invention may be prepared from a variety of substituted natural and unnatural amino acids of formulas 31. The preparation of many of these acids is described in e.g., U.S. Pat. Nos 5,206,235, 5,283,241, 5,284,841, 5,310,737 and 5,317,017. The preparation of these intermediates in racemic form is accomplished by classical methods familiar to those skilled in the art (Williams, R. M. "*Synthesis of Optically Active α-Amino Acids*" Pergamon Press: Oxford, 1989; Vol. 7). Several methods exist to resolve (DL)-

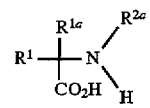

amino acids. One of the common methods is to resolve amino or carboxyl protected intermediates by crystallization of salts derived from optically active acids or amines. Alternatively, the amino group of carboxyl protected intermediates may be coupled to optically active acids by using chemistry described earlier. Separation of the individual diastereomers either by chromatographic techniques or by crystallization followed by hydrolysis of the chiral amide furnishes resolved amino acids. Similarly, amino protected intermediates may be converted to a mixture of chiral diastereomeric esters and amides. Separation of the mixture using methods described above and hydrolysis of the individual diastereomers provides (D) and (L) amino acids. Finally, an enzymatic method to resolve N-acetyl derivatives of (DL)-amino acids has been reported by Whitesides and coworkers in *J. Am. Chem. Soc.*, 111, 6354–6364 (1989).

When it is desirable to synthesize these intermediates in optically pure form, established methods include: (1) asymmetric electrophilic amination of chiral enolates (*J. Am. Chem. Soc.*, 108, 6394–6395, 6395–6397, and 6397–6399 (1986)), (2) asymmetric nucleophilic amination of optically active carbonyl derivatives, (*J. Am. Chem. Soc.*, 114, 1906 (1992); *Tetrahedron Lett.*, 28, 32 (1987)), (3) diastereoselective alkylation of chiral glycine enolate synthons (*J. Am. Chem. Soc.*, 113, 9276 (1991); *J. Org. Chem.*, 54, 3916 (1989)), (4) diastereoselective nucleophilic addition to a chiral electrophilic glycinate synthon (*J. Am. Chem. Soc.*, 108, 1103 (1986)), (5) asymmetric hydrogenation of prochiral dehydroamino acid derivatives (*Asymmetric Synthesis, Chiral Catalysis*; Morrison, J. D., Ed; Academic Press: Orlando, Fla.; Vol 5 (1985)), and (6) enzymatic syntheses (*Angew. Chem. Int. Ed. Engl.*, 17, 176 (1978)).

SCHEME 15

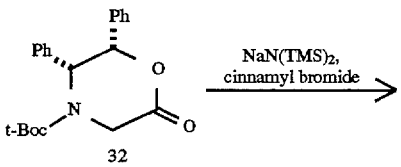

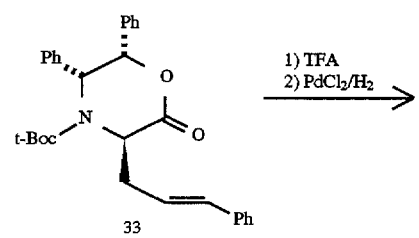

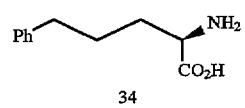

For example, alkylation of the enolate of diphenyloxazinone 32 (*J. Am. Chem. Soc.*, 113, 9276 (1991)) with cinnamyl bromide in the presence of sodium bis(trimethylsilyl) amide proceeds smoothly to afford 33 which is converted into the desired (D)-2-amino-5-phenylpentanoic acid 34 by removing the N-t-butyloxycarbonyl group with trifluoroacetic acid and hydrogenation over a PdCl$_2$ catalyst (Scheme 15).

SCHEME 16

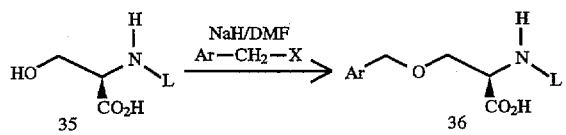

Intermediates of Formula 31 which are O-benzyl-(D)-serine derivatives 36 are conveniently prepared from suitably substituted benzyl halides and N-protected-(D)-serine 35. The protecting group L is conveniently a BOC or a CBZ group. Benzylation of 35 can be achieved by a number of methods well known in the literature including deprotonation with two equivalents of sodium hydride in an inert solvent such as DMF followed by treatment with one equivalent of a variety of benzyl halides (*Synthesis*, 36 (1989)) as shown in Scheme 16.

The O-alkyl-(D)-serine derivatives may also be prepared using an alkylation protocol. Other methods that could be utilized to prepare (D)-serine derivatives of Formula 36 include the acid catalyzed benzylation of carboxyl protected intermediates derived from 35 with reagents of formula ArCH$_2$OC(=NH)CCl$_3$ (O. Yonemitsu et al., *Chem. Pharm. Bull.*, 36, 4244 (1988). Alternatively, alkylation of the chiral glycine enolates (*J. Am. Chem. Soc.*, 113, 9276 (1991); *J. Org. Chem.*, 54, 3916 (1989)) with ArCH$_2$OCH$_2$X where X is a leaving group affords 36. In addition D,L-O-aryl(alkyl) serines may be prepared and resolved by methods described above.

It is noted that in some situations the order of carrying out the foregoing reaction schemes may be varied to facilitate the reaction or to avoid unwanted reaction products.

The utility of the compounds of the present invention as growth hormone secretagogues may be demonstrated by methodology known in the art, such as an assay described by Smith, et al., *Science*, 260, 1640–1643 (1993) (see text of FIG. 2 therein). In particular, the intrinsic growth hormone secretagogue activities of the compounds of the present invention may be demonstrated in this assay. The compounds of the following examples have activity in the aforementioned assay in the range of 0.1 nm to 5 μm.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release and that the growth hormone releasing factor (GRF) stimulates its release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the catabolic side effects or with other pharmaceutically active materials wherein the combination enhances efficacy and minimizes side effects.

Growth promoting and anabolic agents include, but are not limited to, TRH, diethylstilbesterol, estrogens, β-agonists, theophylline, anabolic steroids, enkephalins, E series prostaglandins, retinoic acid, compounds disclosed in U.S. Pat. No. 3,239,345, e.g., zeranol, and compounds disclosed in U.S. Pat. No. 4,036,979, e.g., sulbenox, or peptides disclosed in U.S. Pat. No. 4,411,890.

A still further use of the growth hormone secretagogues of this invention is in combination with other growth hormone secretagogues such as the growth hormone releasing peptides GHRP-6, GHRP-1 as described in U.S. Pat. No. 4,411,890 and publications WO 89/07110, WO 89/07111 and B-HT920 as well as hexarelin and GHRP-2 as described in WO 93/04081 or growth hormone releasing hormone (GHRH, also designated GRF) and its analogs or growth hormone and its analogs or somatomedins including IGF-1 and IGF-2 or α-adrenergic agonists such as clonidine or serotonin 5HTID agonists such as sumitriptan or agents which inhibit somatostatin or its release such as physostigmine and pyridostigmine. For example, a compound of the present invention may be used in combination with IGF-1 for the treatment or prevention of obesity. In addition, a compound of this invention may be employed in conjunction with retinoic acid to improve the condition of musculature and skin that results from intrinsic aging.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses may be summarized as follows: treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treating obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia, treatment of peripheral neuropathies; replacement of growth hormone in stressed patients; treatment of osteochondrody-splasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation; treating malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; stimulation of thymic development and prevention of the age-related decline of thymic function; adjunctive therapy for patients on chronic hemodialysis; treatment of immunosuppressed patients and to enhance antibody response following vaccination; increasing the total lymphocyte count of a human, in particular, increasing the $T_4/T_8$-cell ratio in a human with a depressed $T_4/T_8$-cell ratio resulting, for example, from infection, such as bacterial or viral infection, especially infection with the human immunodeficiency virus; treatment of syndromes manifested by non-restorative sleep and musculoskeletal pain, including fibromyalgia syndrome or chronic fatigue syndrome; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock; and stimulation of wool growth in sheep. Further, the instant compounds are useful for increasing feed efficiency, promoting growth, increasing milk production and improving the carcass quality of livestock. Likewise, the instant compounds are useful in a method of treatment of diseases or conditions which are benefited by the anabolic effects of enhanced growth hormone levels that comprises the administration of an instant compound.

In particular, the instant compounds are useful in the prevention or treatment of a condition selected from the group consisting of: osteoporosis; catabolic illness; immune deficiency, including that in individuals with a depressed $T_4/T_8$ cell ratio; hip fracture; musculoskeletal impairment in the elderly; growth hormone deficiency in adults or in children; obesity; cachexia and protein loss due to chronic illness such as AIDS or cancer; and treating patients recovering from major surgery, wounds or burns, in a patient in need thereof.

In addition, the instant compounds may be useful in the treatment of illnesses induced or facilitated by corticotropin releasing factor or stress- and anxiety-related disorders, including stress-induced depression and headache, abdominal bowel syndrome, immune suppression, HIV infections, Alzheimer's disease, gastrointestinal disease, anorexia nervosa, hemorrhagic stress, drug and alcohol withdrawal symptoms, drug addiction, and fertility problems.

It will be known to those skilled in the art that there are numerous compounds now being used in an effort to treat the diseases or therapeutic indications enumerated above. Combinations of these therapeutic agents some of which have also been mentioned above with the growth hormone secretagogues of this invention will bring additional, complementary, and often synergistic properties to enhance the growth promotant, anabolic and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N. A. T., "Role of Bisphosphonates in Metabolic Bone Diseases" *Trends in Endocrinol. Metab.*, 4, 19–25 (1993). Bisphosphonates with these utilities include alendronate, tiludronate, dimethyl-APD, risedronate, etidronate, YM-175, clodronate, pamidronate, and BM-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 10 mg/kg. of body weight daily are administered to patients and animals, e.g., mammals, to obtain effective release of growth hormone.

The following examples are provided for the purpose of further illustration only and are not intended to be limitations on the disclosed invention.

INTERMEDIATE 1

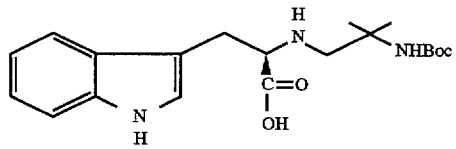

Step A:

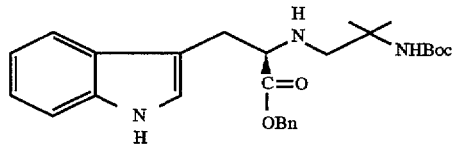

To 5.0 g (16.5 mmole) of the commercially available N-t-BOC-D-tryptophan in 100 mL of chloroform was added 1.80 mL (16.5 mmole) of benzyl alcohol, 0.20 g (1.65 mmole) of 4-N,N-dimethylamino pyridine (DMAP), and 3.20 g of EDC and stirred for 16 h. The reaction mixture was poured into 100 mL of water and the organic layer was separated. The aqueous was further extracted with 2×100 mL of chloroform. The combined organic solution was washed with 50 mL of 10% aqueous citric acid, 100 mL of 10% aqueous sodium bicarbonate solution, dried over anhydrous magnesium sulfate, filtered and concentrated to give a thick oil.

To a solution of this oil in 10 mL of dichloromethane was added 20 mL of trifluoroacetic acid and stirred for 1 h. The reaction mixture was concentrated, basified carefully with saturated aqueous sodium bicarbonate solution, and extracted with chloroform (2×100 mL). The combined organic solution were washed with brine (100 mL), dried over potassium carbonate, filtered, and concentrated to give 5.46 g of the amine as a brown oil which was used without purification.

To 5.46 g of the above product in 100 mL of chloroform was added 3.40 g (22.2 mmole) of HOBT, 4.60 g (22.2 mmole) of N-BOC-α-methyl alanine, and 5.32 g (28.0 mmole) of EDC and stirred for 16 h. The reaction mixture was poured into 100 mL of water and the organic layer was separated. The aqueous was further extracted with 2×100 mL of chloroform. The combined organic solution were washed with 50 mL of 10% aqueous citric acid, 100 mL of 10% aqueous sodium bicarbonate solution, dried over anhydrous magnesium sulfate, filtered and concentrated to give 6.94 g of the product as a thick oil. Flash chromatography (200 g SiO₂; hexane-ethyl acetate as eluent) gave 4.75 g of the desired material as a colorless foam.

¹H NMR (CDCl₃, 200 MHz) δ8.48 (bs, 1H), 7.54 (bd, 1H), 7.38–7.23 (m, 3H), 7.19 (bd, 2H), 7.15–7.00 (m, 1H), 6.90 (d, 1H), 6.86 (d, 1H), 5.06 (bs, 2H), 4.95 (ddd, 1H), 3.30 (2dd, 2H), 1.40 (s, 15H)

Step B:

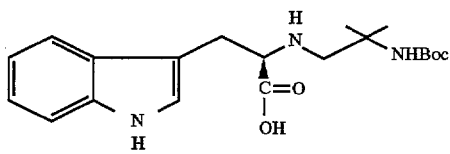

To a solution of 4.75 g of the material from Step A in 100 mL of ethanol was added 1.0 g of 10% Pd/C and stirred at RT under a H₂ balloon for 18 h. The catalyst was filtered off through a pad of celite and washed with ethyl acetate. The filtrate was concentrated to give 2.96 g of the acid as a colorless foam.

¹H NMR (CDCl₃, 200 MHz) δ8.60 (bs, 1H), 7.55 (d, 1H), 7.26–6.90 (m, 3H), 6.88 (bd, 1H), 4.80 (m, 1H), 3.32 (2dd, 2H), 1.37 (s, 3H), 1.35 (s, 12H)

INTERMEDIATE 2

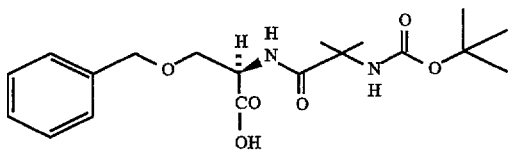

Step A:

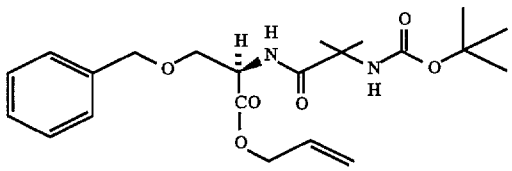

Prepared from N-tBOC-O-benzyl-D-serine and allyl alcohol by the procedure described in Intermediate 1, Step A and subsequent coupling to N-BOC-α-methylalanine to give the desired compound.

¹H NMR (400 MHz, CDCl₃) δ7.25 (s, 5H), 5.8 (m, 1H), 5.2 (dd, 2H), 5.0 (bs., 1H), 4.7 (m, 1H), 4.6 (m, 2H), 4.4 (dd, 2H), 3.9 (dd, 1H), 3.6 (dd, 1H), 1.45 (d, 6H), 1.39 (s, 9H).

Step B:

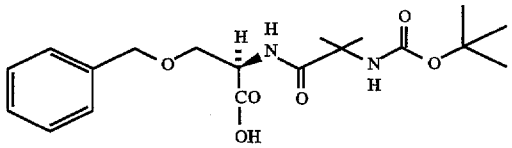

To a stirred solution of the crude intermediate obtained in Step A (6.7 g, 15.9 mmol), tetrakis (triphenylphosphine)- palladium (1.8 g, 0.1 eq) and, triphenyl phosphine (1.25 g, 0.3 eq) was added a solution of potassium-2-ethyl hexanoate (35 mL, 0.5M solution in EtOAc). The reaction mixture was stirred at room temperature under nitrogen atmosphere for 1 h and then diluted with ether (100 mL) and poured into ice-water. The organic layer was separated and the aqueous fraction was acidified with citric acid (20%), then extracted with EtOAc. The EtOAc extracts were washed with brine, dried over magnesium sulfate, filtered and evaporated to give the title compound as a solid.

¹H NMR (400 Hz, CD₃OD) δ7.3 (s, 5H), 4.7 (m, 1H), 4.5 (s, 2H), 4.0 (m, 1H), 3.6 (m, 1H), 1.4 (d, 6H), 1.3 (s, 9H).

INTERMEDIATE 3

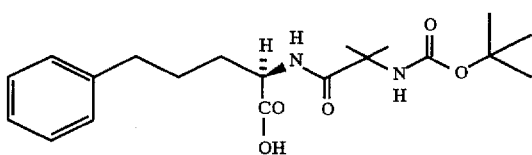

This intermediate was synthesized as described in Step A and B of Intermediate 1, but (2R)-N-t-BOC-5-phenylpentanoic acid (H. K. Chenault et al., *J. Am. Chem. Soc.*, 111, 6354–6364 (1989)) was used in place of N-t-BOC-(D)-Tryptophan.

¹H NMR (CDCl₃, 400 MHz) 7.24–7.20 (m, 2H), 7.15–7.04 (m, 3H), 4.60–4.55 (m, 1H), 2.62–2.55 (m, 2H), 2.00–1.86 (m, 1H), 1.78–1.60 (m, 3H), 1.50 (s, 6H), 1.30 (s, 9H).

EXAMPLE 1

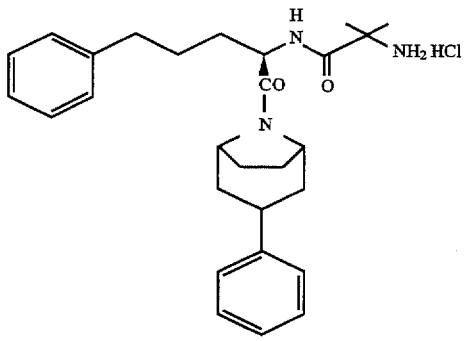

Step A:

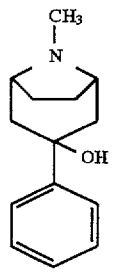

To a solution of tropinone (10.00 g, 71.84 mmol) in anhydrous ether (100 ml) at 0° C, phenyllithium (47.89 ml, 86.2 mmol, 1.8M solution) was added slowly. The cloudy mixture was then heated to reflux for 3.5 hours. The brown solution was cooled to 0° C. and ice water (150 ml) was added. The titled compound (3.75 g) was obtained as a white solid by filtration, washing with water (3×10 ml), hexane (3×10 ml), and drying overnight under vacuum.

¹H NMR (CDCl₃, 400 MHz): 7.53 (d, J=7.5 Hz, 2H), 7.32 (m, 2H), 7.22 (m, 1H), 3.31 (br s, 2H), 2.51 (d, J=Hz, 2H), 2.40 (s, 3H), 2.29 (d, J=7.5 Hz, 2H), 2.04 (m, 2H), 1.80 (d, J=14.6 Hz, 2H), 1.51 (s, 1H).

Step B:

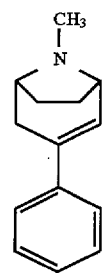

To the intermediate (1.00 g, 4.6 mmol) prepared from Step A, aqueous HBr (48%, 5 ml) was added. The mixture was stirred at 75° C. for 3 hr and at room temperature overnight. Aqueous potassium carbonate was added to adjust the pH to about 10. The aqueous was then extracted with EtOAc (3×30 ml). The combined ethyl acetate layers were washed with brine and dried over sodium sulfate. The titled compound was obtained (0.92 g) and was clean enough for the next step without purification.

¹H NMR (CDCl₃, 400 MHz): 7.37 (m, 2H), 7.30 (m, 2H), 7.23 (m, 1H), 6.25 (m, 1H), 3.53 (m, 2H), 2.88 (m, 1H), 2.48 (s, 3H), 2.25 (m, 3H), 1.97 (m, 1H), 1.65 (m, 1H).

Step C:

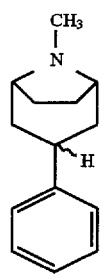

The intermediate (0.357 g, 1.8 mmol) from Step B was hydrogenated at 1 atm with a balloon at room temperature for 4 hr in EtOH (10 ml) and Pd/C (10%, 0.11 g) was used as a catalyst. The titled compound was obtained as a yellow oil (0.346 g) after filtration and evaporation.

¹H NMR (CDCl₃, 400 MHz, 3:1 mixture): 7.27 (m, 4H), 7.15 (m, 1H), 3.25 (m, 2H), 3.05 (m, 1H), 2.49 (m, 2H), 2.28 (s, 3H), 2.03 (m, 2H), 1.67 (m, 2H), 1.48 (m, 2H).

Step D:

To a solution of the intermediate (0.346 g, 1.72 mmol) from Step C in dichloroethane (3 ml) at 0° C., α-chloroethylchloroformate (0.37 ml, 3.44 mmol) was added and the solution was heated to reflux for 1 hr. The solvent was removed and MeOH (3 ml) was added. The solution was refluxed for another 50 min. The MeOH was evaporated and benzene and methylene chloride were added and removed separately to ensure removal of all by-products. The titled compound was obtained as a light yellow solid (0.35 g, 95%) and was clean enough for the next step.

$^1$H NMR (CDCl$_3$, 400 MHz, 3:1 mixture): 9.61 (m, 1H), 7.37 (m, 4H), 7.21 (m, 1H), 4.10 (m, 1H), 3.81 (m, 1H), 3.42 (m, 1H), 3.10 (m, 1H), 2.78 (m, 2H), 2.45 (m, 1H), 2.20 (m, 2H), 1.99 (m, 1H), 1.80 (m, 1H).

Step E:

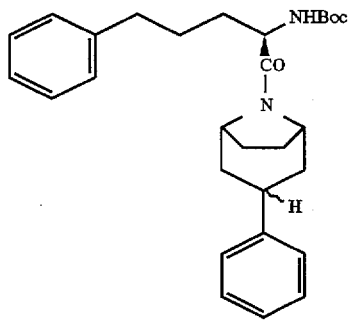

A mixture of the intermediate from Step D (0.15 g, 0.70 mmol), (2R)-N-t-Boc-5-phenylpentanoic acid (0.25 g, 0.84 mmol), EDC (0.20 g, 1.0 mmol), HOBT (0.143 g, 1.0 mmol), and 4-methylmorpholine (0.093 ml, 0.84 mmol) in methylene chloride (20 ml) was stirred at room temperature overnight. The solution was concentrated under vacuum and chromatographed on a flash column (EtOAc:hexane=3:7) to give the titled compound (0.125 g).

$^1$H NMR (CDCl$_3$, 400 MHz, mixture of rotamers): 7.21 (m, 10H), 5.38 (m, 1H), 4.70 (m, 1H), 4.48 (m, 1H), 4.23 (m, 1H), 2.55 (m, 3H), 2.04 (m, 1H), 1.90 (m, 1H), 1.75 (m, 2H), 1.64 (m, 4H), 1.55 (m, 4H), 1.42 (s, 9H).

Step F:

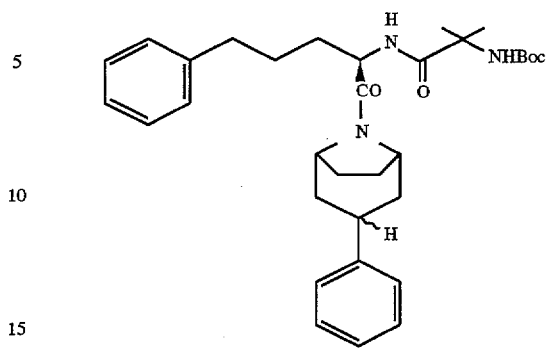

The intermediate from Step E (0.121 g, 0.26 mmol) was stirred with saturated HCl in EtOAc (2.5 ml) at room temperature for 1 hr. The solvent was removed and dried. The residue was mixed with N-Boc-α-methylalanine (0.064 g, 0.31 mmol), EDC (0.075 g, 0.39 mmol), HOBT (0.053 g, 0.39 mmol) and 4-methylmorpholine (0.035 ml, 0.31 mmol) in methylene chloride (10 ml) and stirred at room temperature overnight. The titled compound was obtained by flash column (EtOAc:hexane=4:6) as a gel like solid (0.132 g).

$^1$H NMR (CDCl$_3$, 400 MHz, mixture of rotamers): 7.16 (m, 10H), 5.07 (m, 1H), 4.72 (m, 2H), 4.20 (m, 1H), 3.70 (m, 1H), 2.55 (m, 3H), 2.10 (m, 1H), 1.88 (m, 1H), 1.78 (m, 2H), 1.60 (m, 4H), 1.50 (m, 19H).

Step G:

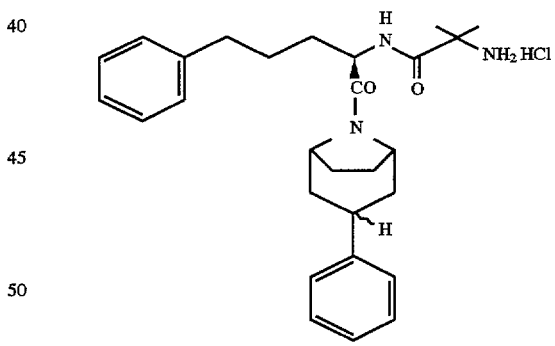

The intermediate (0.132 g, 2.4 mmol) from Step F was stirred with HCl in dioxane (4M, 2 ml) at room temperature for 2 hr. The solvent was removed. The title compound was obtained as a white solid (0.124 g).

$^1$H NMR (CD$_3$OD, 400 MHz, mixture of rotamers): 7.20 (m, 10H), 4.73 (m, 1H), 4.60 (m, 1H), 4.32 (m, 1H), 3.66 (m, 1H), 2.71 (m, 2H), 2.54 (m, ½H), 2.42 (m, 1H), 2.11 (m, ½H), 1.73 (m, 9H), 1.63 (m, 6H). FAB-MS: 448.3 (M+1).

EXAMPLE 2

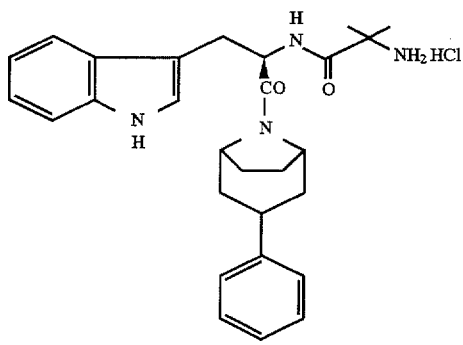

Step A:

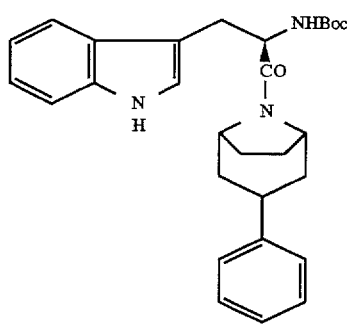

The title compound (0.115 g) was obtained following the procedure in Example 1, Step E starting with the amine hydrochloride salt (0.151 g, 0.7 mmol) from Step D and N-Boc-D-tryptophan (0.258 g, 0.85 mmol).

Step B:

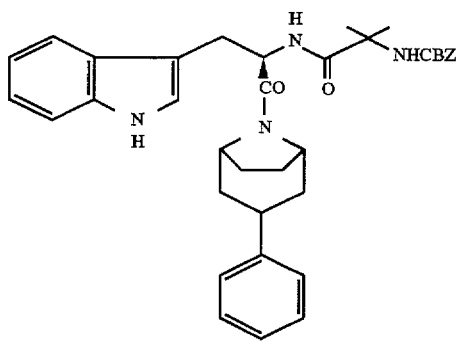

The titled compound (0.04 g) was obtained followed the procedure described in Example 1, Step F starting with the titled compound from Step A (0.11 g, 0.23 mmol) and N-CBZ-α-methylalanine (0.066 g, 0.27 mmol).

Step C:

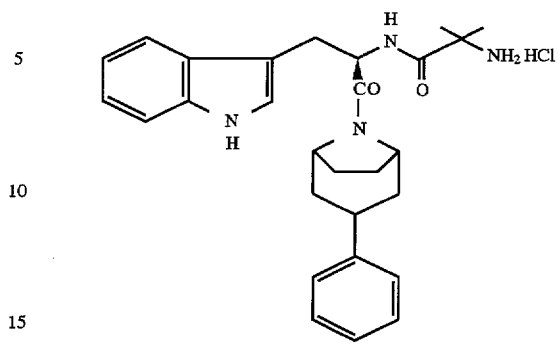

The titled compound from Step B (0.04 g) was hydrogenated in EtOH at 1 atm at rt using Pd/C as catalyst for 20 hr. The mixture was filtered and the filtrate was concentrated in vacuo. The resulting amine was treated with 1M HCl in MeOH and purified by MPLC (LH20, MeOH) to give the titled compound (0.025 g).

$^1$H NMR (CD$_3$OD, 400 MHz, mixture of rotamers): 8.32 (m, 1H), 7.60 (m, 1H), 7.43 (m, 1H), 7.16 (m, 7H), 6.90 (m, 1H), 5.20 (m, 0.5H), 4.60 (m, 0.5H), 4.38(m, 1H), 3.80 (m, 1H), 3.22 (m, 2H), 2.75 (m, 1H), 2.49 (m, 1H), 2.25 (m, 1H), 2.04 (m, 1H), 1.60 (m, 6H), 1.30 (m, 5H), 0.60 (m, 1H). FAB-MS: 459.2 (M+1).

EXAMPLE 3

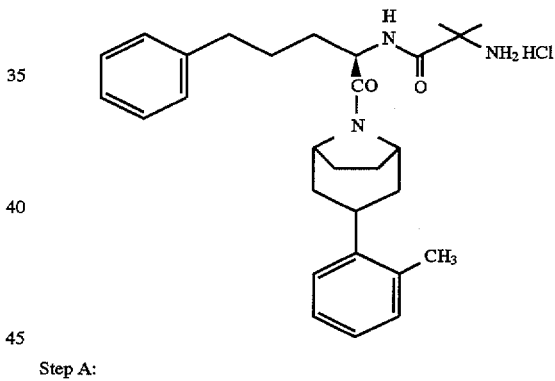

Step A:

To a solution of tropinone (13.92 g, 0.1 mol) in THF 100 ml at −78° C., KN(TMS)2 (0.12 mol, 240 ml, 0.5M) was added slowly. The solution was stirred at −78° C. for 1 hr. A solution of N-phenyltrifluoromethane-sulfonamide (42.87 g, 0.12 mol) in THF (50 ml) was added slowly. The solution was then gradually warmed up to room temperature and stirred for another 3 hr. Saturated aqueous ammonium chloride was added and the THF was removed. The aqueous was extracted with EtOAc (3×100 ml). The combined EtOAc layers were washed with brine and dried over sodium sulfate. The titled compound was obtained as a brown oil (16.42 g) after flash chromatography (EtOAc:MeOH- 9:1).

Step B:

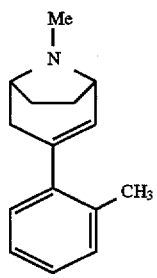

To a slurry of CuI (2.80 g, 14.5 mmol) in THF (20 ml) at 0° C., a solution of o-tolymagnesium bromide (20 mmol, 20 ml, 1M) was added slowly. The mixture was stirred at 0° C. for 30 min. A solution of the titled compound from Step A (1.00 g, 3.7 mmol) in THF (20 ml) was added dropwise. The whole was then stirred at room temperature for 20 hr. The mixture was filtered through Celite and the filtrate was concentrated. The titled compound was obtained as a solid (0.95 g) after flash chromatography (EtOAc:MeOH=9:1).

Step C:

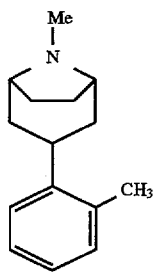

Sodium (20 mg) was added to a dry three neck flask under nitrogen and it was dissolved in the liquid ammonia generated via a Cold Finger at −78° C. A solution of the titled compound from Step B (0.095 g, 0.44 mmol) in THF (5 ml) was added to the mixture and the blue color disappeared. The solution was stirred for 20 min at −78° C. and EtOH (5 ml) was added slowly. The solvent was removed and dried. The titled compound was obtained (0.078 g) and was pure enough for next step.

Step D:

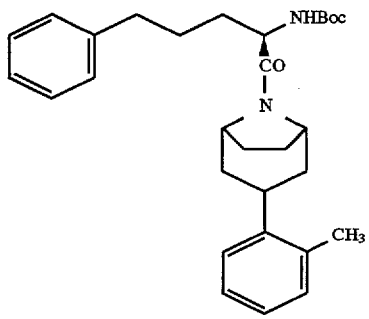

The titled compound from Step C (0.072 g, 0.33 mmol) was converted to the demethylated hydrochloride salt using the procedure described in Example 1, Step D. The resulting salt was coupled with (2R)-N-t-Boc-5-phenylpentanoic acid (0.12 g, 0.4 mmol) to give the titled compound, using the procedure described in Example 1, Step E.

Step E:

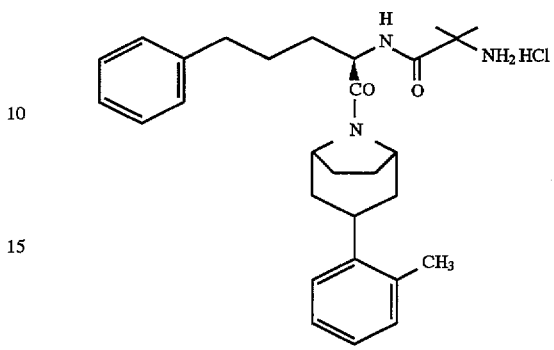

The titled compound from Step D (0.023 g) was treated with HCl in EtOAc for 30 min. The HCl was removed. The residue was coupled with N-Boc-α-methylalanine using the procedure described in Example 1, Step F. The titled compound (0.018 g) was obtained after chromatography (EtOAc:hexane=3:7) and deprotection using the procedure from Example 1, Step G.

$^1$H NMR (CD$_3$OD, 400 MHz, mixture of rotamers): 7.15 (m, 9H), 4.70 (m, 2H), 4.57 (m, 1H), 4.22 (m, 1H), 3.48 (m, 1H), 2.69 (m, 2H), 2.35 (m, 3H), 2.15 (m, 1H), 1.97 (m, 2H), 1.75 (m, 17H). FAB-MS: 462.1 (M+1).

EXAMPLE 4

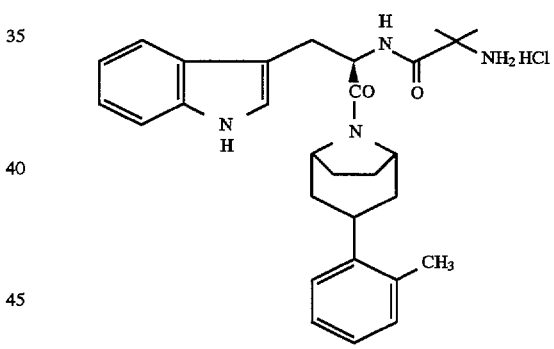

Step A:

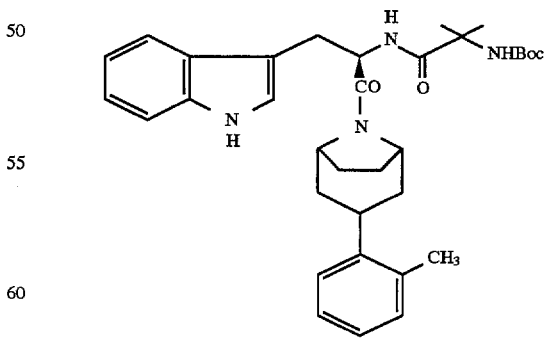

The titled compound (0.016 g) from Example 3, Step C was demethylated using the procedure described in Example 1, Step D. The resulting hydrochloride salt was coupled with Intermediate 1 using the procedure described in Example 1, Step F. The titled compound (0.008 g) was obtained after chromatography (EtOAc:hexane=4:6).

Step B:

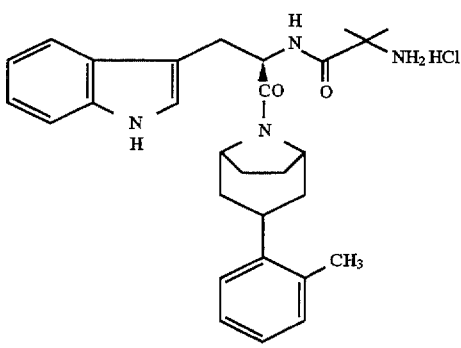

The titled compound (2 mg) was obtained after treatment of the titled compound (8 mg), from Step A, with HCl in EtOAc and a LH-20 purification.

¹H NMR (CD₃OD, 400 MHz, mixture of rotamers): 8.32 (m, 1H), 7.60 (m, 1H), 7.37 (m, 1H), 7.28 (m, 1H), 7.08 (m, 5.5H), 6.23 (m, 0.5H), 5.08 (m, 0.5H), 4.90 (m, 0.5H), 4.61 (m, 0.5H), 4.48 (m, 0.5H), 4.40 (m, 1H), 3.80 (m, 1H), 3.45 (m, 1H), 3.22 (m, 2H), 3.15 (m, 1H), 2.22 (s, 3H), 1.50 (m, 14H), 0.45 (m, 1H). FAB-MS: 473.3 (M+1).

EXAMPLE 5

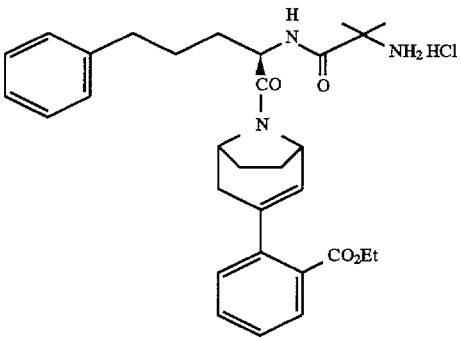

Step A:

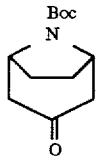

Tropinone (10.14 g, 72.8 mmol) was demethylated using the procedure described in Example 1, Step D. The resulting hydrochloride salt was dissolved in 2-propanol (100 ml). t-Boc anhydride (31.80 g, 0.14 mol) in 2-propanol (20 ml) and aqueous NaOH (5.82 g, 0.14 mol, 20 ml) were added to the solution. The mixture was stirred at room temperature for 20 hr. The 2-propanol was removed via vacuum. The aqueous was then extracted with EtOAc (3×150 ml). The combined EtOAc layers were washed with brine, and dried over sodium sulfate. The titled compound was obtained as a white solid (13.01 g).

Step B:

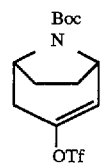

To a solution of the titled compound (5.00 g, 22 mmol), from Step A, in THF (50 ml) at −78° C., KN(TMS)2 (26.7 mmol, 0.5M in toluene) was added slowly. The solution was stirred at −78° C. for 30 min. A solution of N-phenyltrifluoromethane sulfonamide (9.52 g, 26.67 mmol) in THF (50 ml) was added. The whole was stirred at −78° C. for 2 hr. Saturated aqueous ammonium chloride (50 ml) was added and the THF was removed. The aqueous was then extracted with EtOAc (3×60 ml). The combined EtOAc layers were washed with 1N KOH (50 ml), brine and dried over sodium sulfate. The titled compound was obtained as colorless liquid (7.29 g).

Step C:

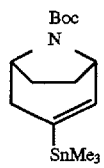

To a solution of the titled compound (7.20 g, 20 mmol), from Step B, in THF (70 ml), hexamethylditin (6.0 g, 18.3 mmol), LiCl (5.30 g, 125 mmol), and tetrakis (triphenylphosphine)palladium (0) (2.33 g, 2 mmol) were added gradually. The mixture was stirred at 60° C. under nitrogen for 1 hr. The color of the solution changed from yellow to dark brown. Buffer solution (pH-7) was added and THF was removed. The aqueous was extracted with EtOAc (3×50 ml). The combined EtOAc layers were washed with brine and dried over sodium sulfate. The titled compound was obtained as a colorless oil (5.36 g) after flash chromatography (EtOAc:hexane=5:95).

Step D:

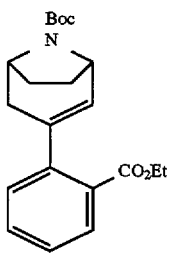

A mixture of the titled compound (3.00 g, 8.07 mmol) from Step C, ethyl 2-bromobenzoate (3.69 g, 16 mmol), and tetrakis(triphenylphosphine)palladium (0) (0.93 g, 0.8 mmol) in dioxane (40 ml) was heated to reflux under nitrogen for 20 hr. Water (50 ml) was added. The aqueous was extracted with EtOAc (3×50 ml). The combined EtOAc layers were washed with brine and dried over sodium sulfate. The titled compound was obtained as an oil (0.40 g) after flash chromatography (EtOAc:hexane=1:9). The recovered starting material was resubmitted for another cycle.

After two cycles more of the titled compound (0.82 g) was obtained.

Step E:

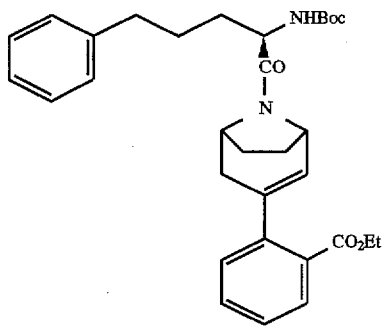

The title compound from Step D (0.25 g) was treated with HCl in EtOAc for 60 min. After removal the HCl solution, the residue was coupled with (2R)-N-t-Boc-phenylpentanoic acid (0.25 g, 0.84 mmol) using the procedure described in Example 1, Step E. The titled compound was obtained (0.34 g) after flash chromatography (EtOAc:hexane=3:7).

Step F:

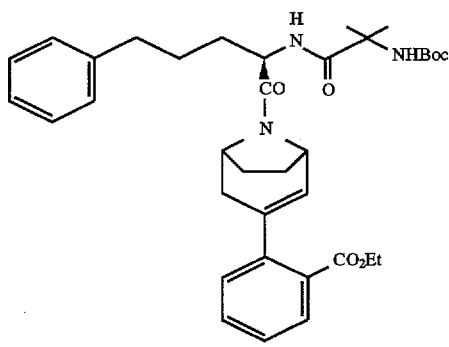

The titled compound from Step E (0.34 g) was treated with HCl in EtOAc for 1 hr. After removal of the HCl solution the residue was coupled with N-Boc-α-methylalanine (0.16 g, 0.77 mmol) using the procedure described in Example I, Step F. The titled compound (0.354 g) was obtained after chromatography (EtOAc:hexane=4:6).

Step G:

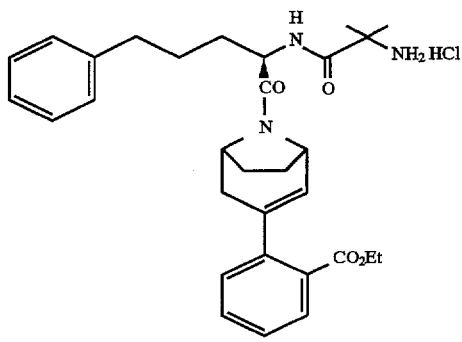

The titled compound (24 mg) was obtained from the titled compound (39 mg) from Step G using the procedure described in Example 1, Step F.

$^1$H NMR(CD$_3$OD, 400 MHz, mixture of rotamers): 7.75 (m, 1H), 7.42 (m, 1H), 7.35 (m, 1H), 7.26 (m, 1H), 7.19 (m, 3H), 7.09 (m, 0.5H), 6.92 (m, 0.5H), 5.70 (m, 0.7H), 5.5 (m, 0.3H), 4.72 (m, 3H), 4.50 (m, 0.5H), 4.39 (m, 0.5H), 4.30 (m, 2H), 3.10 (m, 0.3H), 2.90 (m, 0.7H), 2.68 (m, 2H), 2.15 (m, 5H), 1.80 (m, 6H), 1.60 (m, 6H), 1.34 (m, 3H). FAB-MS: 518.2 (M+1).

EXAMPLE 6

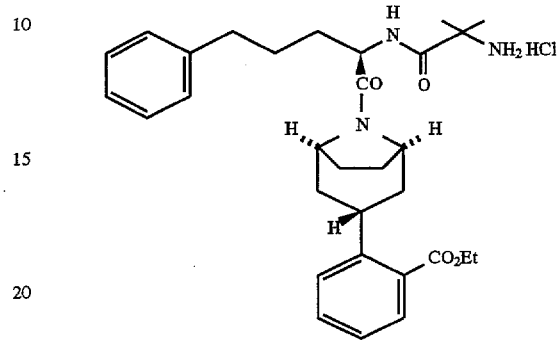

Step A:

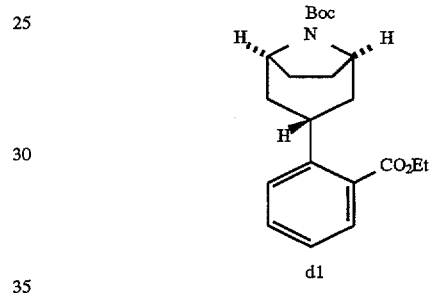

d1

The titled compound (0.67 g) from Example 5, Step D, was hydrogenated at 1 atm in MeOH at room temperature using Pd/C as a catalyst. A mixture of the two isomers (0.65 g) was obtained after filtration and evaporation. The mixture was separated by MPLC (EtOAc:hexane=1:9) to give isomer 1 (d1, 183.9 mg), isomer 2 (d2, 46.8 mg) and a mixture of d1+d2 (0.35 g). X-Ray quality crystals of d1 were crystallized from hexane. X-Ray analysis showed d1 to have the phenyl group oriented trans- to the ethyl bridge.

Step B:

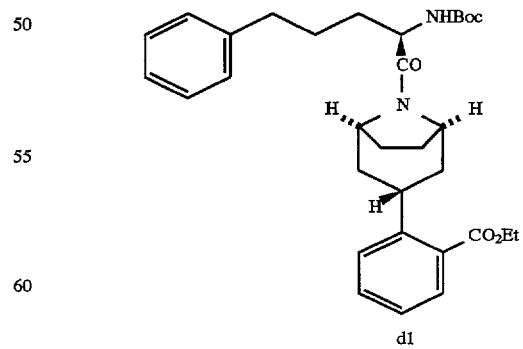

d1

The titled compound (d1, 0.10 g, 0.28 mmol) from Step A was converted to the titled compound (0.123 g) using the procedure described in Example 5, Step E.

Step C:

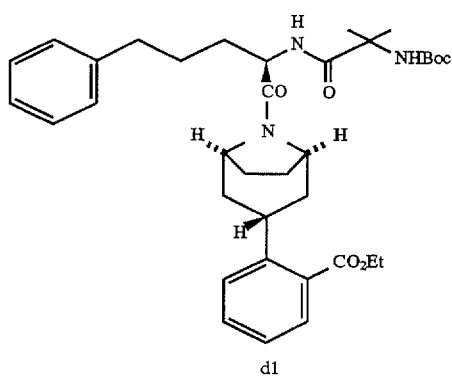

The titled compound (0.114 g) was obtained from the titled compound (0.12 g) from Step B using the procedure described in Example 5, Step F.

Step D:

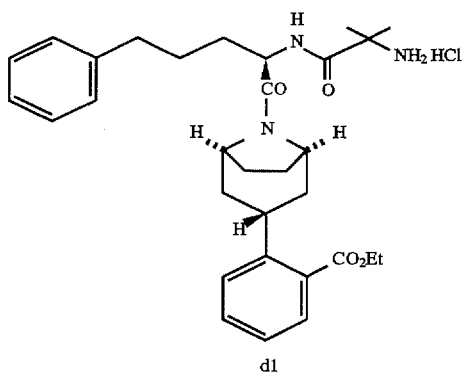

The titled compound (25 mg) was obtained from the titled compound (39 mg) from Step C using the procedure described in Example 5, Step G.

$^1$H NMR (CD$_3$OD, 400 MHz, mixture of rotamers): 7.73 (m, 1H), 7.55 (m, 1H), 7.48 (m, 1H), 7.28 (m, 6H), 4.65 (m, 2.5H), 4.38 (m, 2H), 4.18 (m, 1.5H), 2.68 (m, 2H), 2.25 (m, 1H), 1.80 (m, 13H), 1.60 (m, 6H), 1.40 (m, 3H). FAB-MS: 520.2 (M+1).

EXAMPLE 7

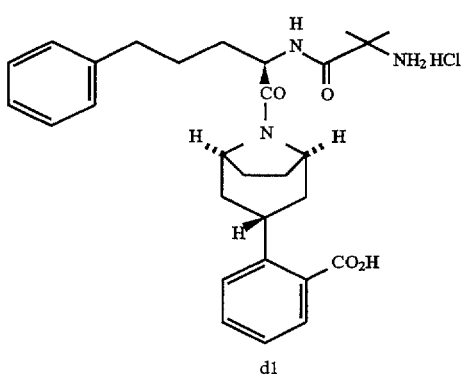

Step A:

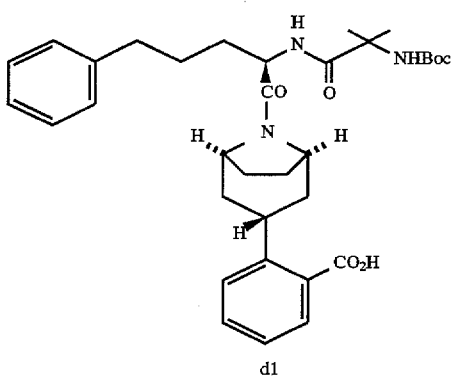

The titled compound (75 mg, 0.12 mmol), from Example 6, Step C, was treated with aqueous NaOH (2 eq, 10 mg) in EtOH for 5 days. EtOH was removed and the aqueous was adjusted pH-3.5. The titled compound (68 mg) was obtained after extraction with EtOAc and evaporation.

Step B:

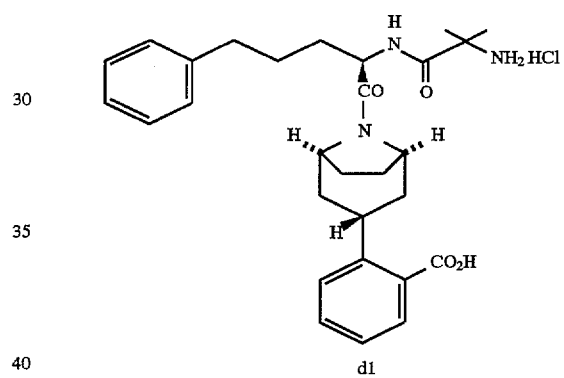

The titled compound (20 mg) was obtained from the titled compound (25 mg) from Step A using the procedure described in Example 5, Step G.

$^1$H NMR (CD$_3$OD, 400 MHz, mixture of rotamers): 7.68 (m, 1H), 7.48 (m, 1H), 7.40 (m, 1H), 7.20 (m, 6H), 4.62 (m, 2.5H), 4.18 (m, 1.5H), 2.69 (m, 2H), 2.20 (m, 1H), 1.80 (m, 13H), 1.60 (m, 6H). FAB-MS: 492.2 (M+1).

EXAMPLE 8

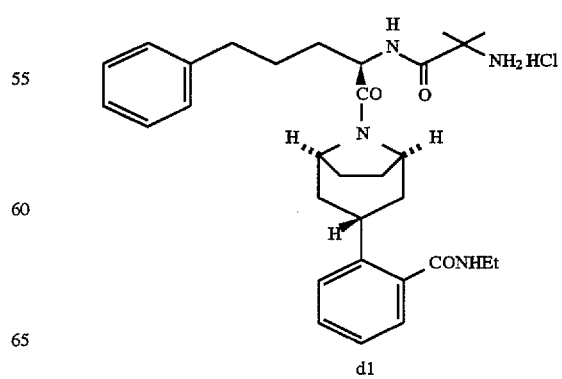

Step A:

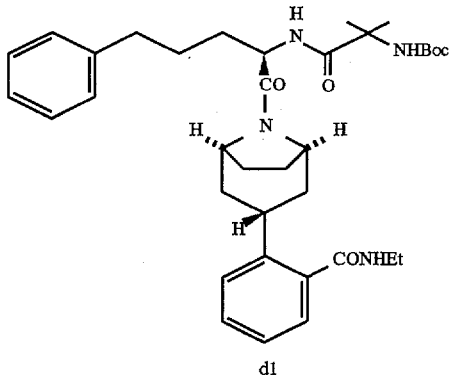

d1

The titled compound (39 mg, 0.06 mmol), from Example 7, Step A, was coupled with ethylamine hydrochloride salt using the procedure described in Example 1, Step E. The titled compound (28.6 mg) was obtained after flash chromatography (EtOAc).

Step B:

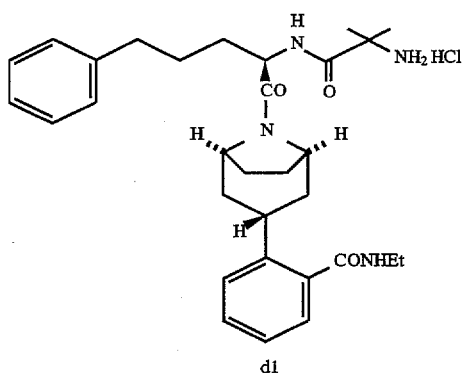

d1

The titled compound (20 mg) was obtained from the titled compound (30 mg) from Step A using the procedure described in Example 5, Step G.

$^1$H NMR (CD$_3$OD, 400 MHz, mixture of rotamers): 8.49 (m, 1H), 7.49 (m, 1H), 7.38 (m, 1H), 7.25 (m, 7H), 4.70 (m, 3H), 4.20 (m, 1H), 3.60 (m, 1H), 3.41 (m, 2H), 2.70 (m, 2H), 2.27 (m, 1H), 1.80 (m, 13H), 1.62 (m, 6H), 1.25 (m, 3H). FAB-MS: 519.2 (M+1).

EXAMPLE 9

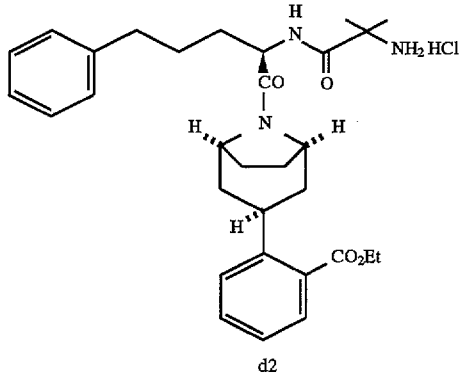

d2

Step A:

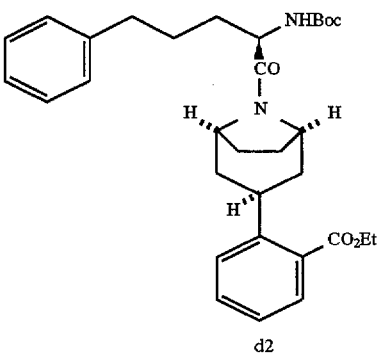

d2

The titled compound (47.5 mg) was obtained from the titled compound (40 mg, 0.11 mmol, d2) from Example 6, Step A using the procedure described in Example 6, Step B.

Step B:

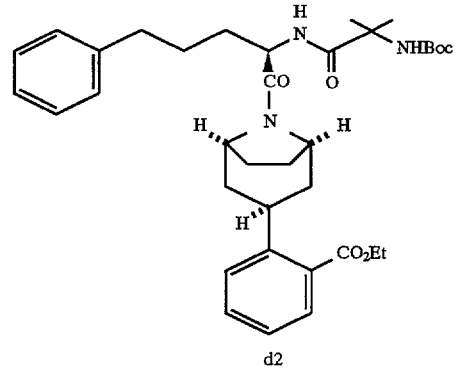

d2

The titled compound (32 mg) was obtained from the titled compound (47 mg) from Step A using the procedure described in Example 6, Step C.

Step C:

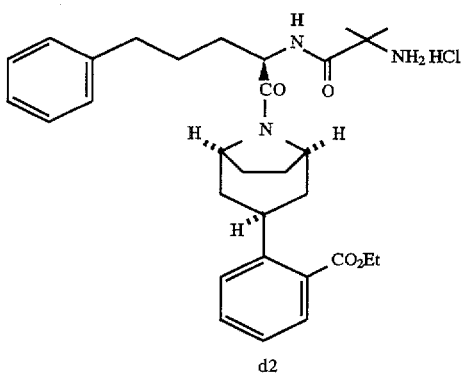

The titled compound (9 mg) was obtained from the titled compound (14 mg) from Step B using the procedure described in Example 6, Step D.

$^1$H NMR (CD$_3$OD, 400 MHz, mixture of rotamers): 7.69 (m, 1H), 7.50 (m, 2H), 7.18 (m, 6H), 4.70 (m, 2.5H), 4.31 (m, 2.5H), 3.30 (m, 1H), 2.69 (m, 2H), 2.48 (m, 1H), 2.12 (m, 1H), 1.80 (m, 8H), 1.60 (m, 6H), 1.50 (m, 5H), 1.37 (m, 3H). FAB-MS: 520.2 (M+1).

EXAMPLE 10

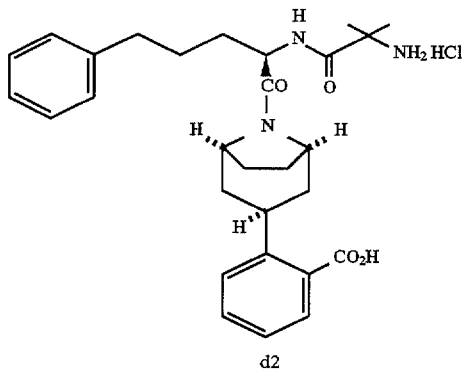

Step A:

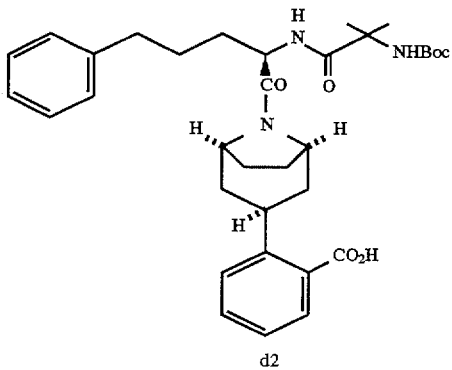

The titled compound (14 mg) was obtained from the titled compound (18 mg) from Example 9, step B using the procedure described in Example 8, Step A.

Step B:

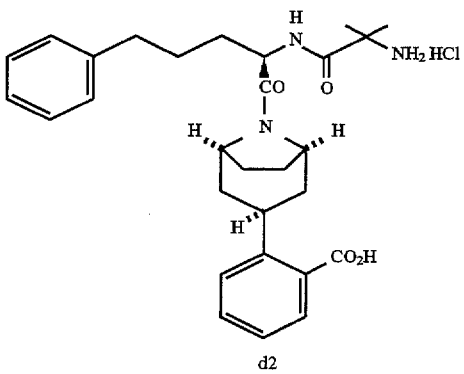

The title compound (11 mg) was obtained from the title compound (14 mg) from Step A using the procedure described in Example 5, Step G.

$^1$H NMR (CD$_3$OD, 400 MHz, mixture of rotamers): 7.40 (m, 9H), 4.65 (m, 2H), 4.35 (m, 1H), 3.50 (m, 0.5H), 3.25 (m, 0.5H), 2.61 (m, 4H), 1.80 (m, 14H), 1.60 (s, 6H). FAB-MS: 492.1 (M+1).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula:

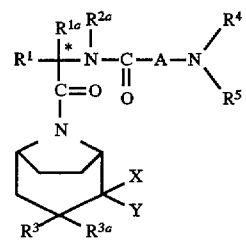

wherein:

R$^1$ is selected from the group consisting of:
C$_1$–C$_{10}$ alkyl, aryl, aryl(C$_1$–C$_6$ alkyl), (C$_3$–C$_7$ cycloalkyl)(C$_1$–C$_6$ alkyl)-, (C$_1$–C$_5$ alkyl)-K—(C$_1$–C$_5$ alkyl)-, aryl(C$_0$–C$_5$ alkyl)-K—(C$_1$–C$_5$ alkyl)-, and (C$_3$–C$_7$ cycloalkyl)(C$_0$–C$_5$ alkyl)-K—(C$_1$–C$_5$ alkyl)-, where K is —O—, —S(O)$_m$—, —N(R$^2$)C(O)—, —C(O)N (R²)—, —OC(O)—, —C(O)O—, —CR²=CR²—, or —C≡C—, where aryl is selected from: phenyl, naphthyl, indolyl, quinolinyl, isoquinolinyl, azaindolyl, pyridyl, benzothienyl, benzofuranyl, thiazolyl, and benzimidazolyl, and R² and alkyl may be further substituted by 1 to 9 halogen, —S(O)$_m$R$^{2a}$, 1 to 3 of —OR$^{2a}$ or —C(O)OR$^{2a}$, and aryl may be further substituted by 1 to 3 of $C_1$-$C_6$ alkyl, 1 to 3 of halogen, 1 to 2 of —OR², methylenedioxy, —S(O)$_m$R², 1 to 2 of —CF₃, —OCF₃, nitro, —N(R²)C(O)(R²), —C(O)OR², —C(O)N(R²)(R²), -1H-tetrazol-5-yl, —SO₂N(R²)(R²), —N(R²)SO₂ phenyl, or —N(R²)SO₂R²;

R$^{1a}$ is hydrogen, or $C_1$-$C_6$ alkyl optionally substituted by phenyl;

R² is selected from: hydrogen, $C_1$-$C_6$ alkyl, and $C_3$-$C_7$ cycloalkyl, and where two $C_1$-$C_6$ alkyl groups are present on one atom, they may be optionally joined to form a $C_3$-$C_8$ cyclic ring, optionally including oxygen, sulfur or NR$^{3a}$;

R$^{2a}$ is hydrogen, or $C_1$-$C_6$ alkyl optionally substituted by phenyl;

R³ is hydrogen, or —(CH₂)$_r$aryl wherein aryl is selected from the group consisting of:

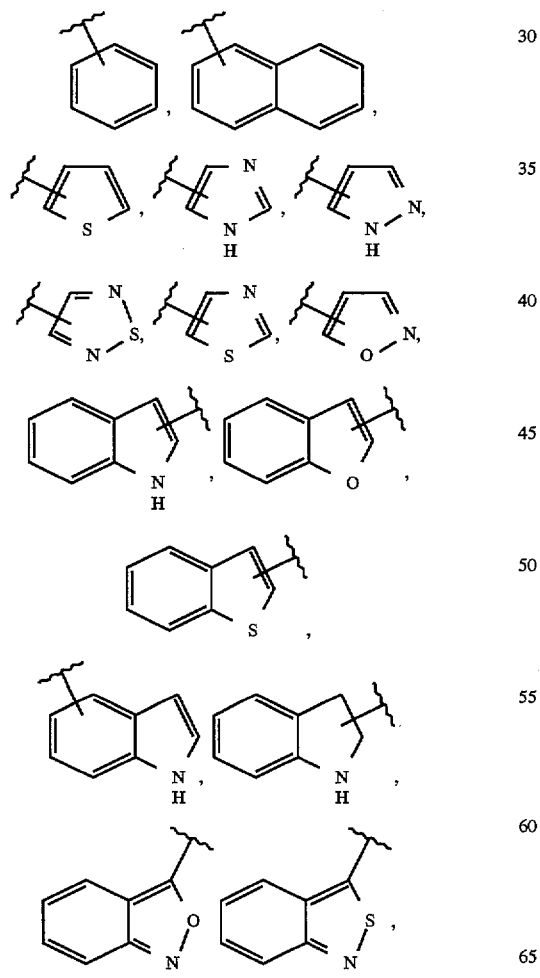

-continued

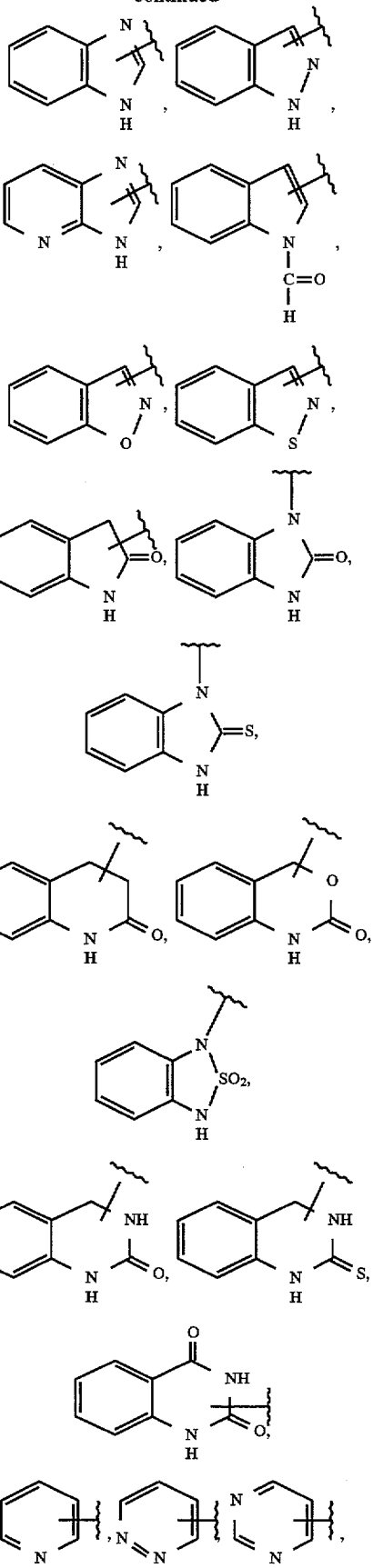

-continued

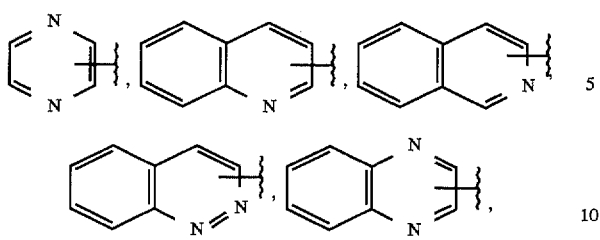

where the aryl is attached to the piperidine ring at an available carbon or nitrogen atom of the aryl, and where the aryl is optionally substituted on at least one available carbon or nitrogen atom by —$R^8$, wherein $R^8$ is independently selected from the group consisting of: hydrogen, $C_1$–$C_6$ alkyl, halogen, —$OR^6$, —$NHSO_2CF_3$, —$(CH_2)_rOR^6$, —$(CH_2)_rN(R^2)(R^6)$, —$(CH_2)_r(R^6)$, $CH_2)_rC(O)OR^6$—$(CH_2)_rOC(O)R^6$, —$(CH_2)_rC(O)R^6$, —$(CH_2)_rC(O)N(R^2)(R^2)$, —$(CH_2)_rC(O)N(R^2)(R^6)$, —$(CH_2)_rN(R^6)C(O)R^6$, —$(CH_2)_rN(R^6)C(O)OR^6$, —$(CH_2)_rN(R^2)C(O)N(R^2)(R^2)$, —$(CH_2)_rN(R^6)C(O)N(R^2)(R^6)$, —$(CH_2)_rN(R^6)SO_2R^6$, —$(CH_2)_rOC(O)N(R^2)(R^6)$, —$(CH_2)_rOC(O)N(R^2)(R^2)$, —$(CH_2)_rSO_2N(R^2)(R^6)$, —$(CH_2)_rSO_2N(R^2)(R^2)$, —$(CH_2)_rSO_2NHC(O)R^6$, —$(CH_2)_rSO_2NHC(O)OR^6$, —$(CH_2)_rC(O)NHC(O)N(R^2)(R^6)$, —$(CH_2)_rC(O)NHC(O)N(R^2)(R^2)$, —$(CH_2)_rC(O)NHC(O)OR^6$, —$(CH_2)_rCONHSO_2R^6$, —$(CH_2)_rCONHSO_2N(R^2)(R^2)$, —$(CH_2)_rCONHSO_2N(R^2)(R^6)$, —$(CH_2)_rN(R^6)SO_2N(R^2)(R^2)$, —$(CH_2)_rN(R^6)SO_2N(R^2)(R^6)$, and —$(CH_2)_rS(O)_mR^6$;

$R^{3a}$ is selected from: hydrogen, and $C_1$–$C_6$ alkyl;

or $R^{3a}$ and one of X and Y may be joined to form a double bond;

or $R^3$ and $R^{3a}$ together may form a spiro system of the formula:

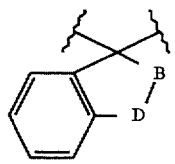

wherein B and D are independently selected from:
—$C(R^2)(R^8)$—, —$C(O)$—, —$O$—, —$S(O)_m$—, and —$NR^8$—, provided that if one of B or D is —$O$—, —$S(O)_m$—, and —$NR^8$—, then the other of B and D is not —$O$—, —$S(O)_m$—, or —$NR^8$—, wherein $R^8$ is as defined above with the option that if an $R^8$ group is present in both B and D such groups may be joined to form a double bond;

$R^4$ and $R^5$ are independently selected from:
hydrogen, $C_1$–$C_6$ alkyl, and substituted $C_1$–$C_6$ alkyl, wherein the substituents are selected from:

1 to 5 halo, 1 to 3 hydroxy, 1 to 3 $C_1$–$C_{10}$ alkanoyloxy, 1 to 3 $C_1$–$C_6$ alkoxy, phenyl, phenoxy, 2-furyl, $C_1$–$C_6$ alkoxycarbonyl, —$S(O)_m(C_1$–$C_6$ alkyl); or $R^4$ and $R^5$ can be taken together to form —$(CH_2)_dL_a(CH_2)_e$— where $L_a$ is —$C(R^2)_2$—, —$O$—, —$S(O)_m$— or —$N(R^2)$—, d and e are independently 1 to 3 and $R^2$ is as defined above;

$R^6$ is hydrogen, $C_1$–$C_6$ alkyl, or $(CH_2)_v$aryl, wherein the alkyl and $(CH_2)_v$ groups may be optionally substituted by 1–2 —$O(R^2)$, —$S(O)_mR^2$, 1H-tetrazol-5-yl, —$C(O)OR^2$, —$C(O)N(R^2)(R^2)$, —$SO_2N(R^2)(R^2)$, or —$N(R^2)C(O)N(R^2)(R^2)$, and where aryl is selected from:

phenyl, naphthyl, pyridyl, 1H-tetrazol-5-yl, triazolyl, imidazolyl, indolyl, thiazolyl, pyrazolyl, thiadiazolyl, imidazolone-1-yl, oxadiazolyl, benzimidazol-2-yl, triazolinone-yl, quinolinyl, isoquinolinyl, and wherein the aryl is optionally substituted with 1 to 2 halogen, 1 to 2 —$R^2$, —$OR^2$, or —$N(R^2)(R^2)$;

A is:

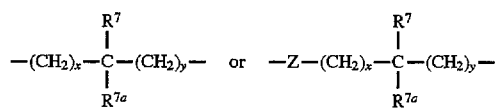

where x and y are independently 0, 1, 2 or 3;

Z is N—$R^{6a}$ or O, where $R^{6a}$ is hydrogen or $C_1$–$C_6$ alkyl;

$R^7$ and $R^{7a}$ are independently selected from: hydrogen, $C_1$–$C_6$ alkyl, trifluoromethyl, phenyl, and substituted $C_1$–$C_6$ alkyl where the substituent is selected from: imidazolyl, phenyl, naphthyl, indolyl, p-hydroxyphenyl, —$OR_2$, —$S(O)_mR^2$, —$C(O)OR^2$, $C_3$–$C_7$ cycloalkyl, —$N(R^2)(R^2)$, and —$C(O)N(R^2)(R^2)$, or $R^7$ and $R^{7a}$ may independently be joined to one or both of $R^4$ and $R^5$ groups to form alkylene bridges between the terminal nitrogen and the alkyl portion of the $R^7$ or $R^{7a}$ groups, wherein the bridge contains 1 to 5 carbons atoms, or $R^7$ and $R^{7a}$ can be joined to one another to form a $C_3$–$C_7$ cycloalkyl;

X is selected from the group consisting of: hydrogen, —$C\equiv N$, —$(CH_2)_qN(R^6)C(O)R^6$, —$(CH_2)_qN(R^6)SO_2R^6$, —$CH_2)_qN(R^6)C(O)N(R^2)(R^6)$—$(CH_2)_qC(O)N(R^2)(R^2)$, —$(CH_2)_qC(O)N(R^2)(R^6)$—$(CH_2)_qC(O)OR^6$, —$CH_2)_qOR^6$, —$(CH_2)_qOC(O)R^6$, —$(CH_2)_qOC(O)N(R^2)(R^6)$—$(CH_2)_qOC(O)N(R^2)(R^2)$, —$(CH_2)_qC(O)R^6$, —$(CH_2)_qN(R^6)C(O)OR^6$, $(CH_2)_qN(R^6)SO_2N(R^2)(R^6)$, $(CH_2)_qN(R^6)SO_2N(R^2)(R^2)$ and —$(CH_2)_qS(O)_mR^6$, where an $R^2$, and the $(CH_2)_q$ and group may be optionally substituted by 1 to 2 $C_1$–$C_4$ alkyl, hydroxyl, $C_1$–$C_4$ lower alkoxy, carboxyl, —$CONH_2$, —$S(O)_mCH_3$, carboxylate $C_1$–$C_4$ alkyl ester, or 1H-tetrazol-5-yl, and where aryl is selected from: phenyl, naphthyl, quinolinyl, isoquinolinyl, pyridyl, thiazolyl, and 1H-tetrazol-5-yl, and where the aryl is optionally substituted by 1 to 3 halogen, 1 to 3 —$OR^2$, —$CON(R^2)(R^2)$, —$C(O)OR^2$, 1 to 3 $C_1$–$C_4$ alkyl, —$S(O)_mR^2$, or 1H-tetrazol-5-yl;

Y is selected from the group consisting of:
hydrogen, $C_1$–$C_{10}$ alkyl, —$(CH_2)_t$aryl, —$(CH_2)_q$ ($C_3$–$C_7$ cycloalkyl), —$(CH_2)_q$—K—($C_1$–$C_6$ alkyl), —$(CH_2)_q$—K—$(CH_2)_t$aryl, —$(CH_2)_q$—K—$(CH_2)_t$ ($C_3$–$C_7$ cycloalkyl where K is O, $S(O)_m$, $C(O)NR^2$, CH=CH, C≡C, $N(R^2)C(O)$, $C(O)NR^2$, C(O)O, or OC(O), and where the alkyl, $R^2$, $(CH_2)_q$ and $(CH_2)_t$ groups are optionally substituted by $C_1$–$C_4$ alkyl, hydroxyl, $C_1$–$C_4$ lower alkoxy, carboxyl, —$CONH_2$ or carboxylate $C_1$–$C_4$ alkyl esters, and where aryl is selected from: phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrrazinyl, and isothiazolyl, and where the aryl is optionally substituted by 1 to 3 halogen, 1 to 3 —OR$^2$, —C(O)OR$^2$, —C(O)N(R$^2$)(R$^2$), nitro, cyano, benzyl, 1 to 3 C$_1$–C$_4$ alkyl, —S(O)$_m$R$^2$, or 1H-tetrazol-5-yl;

m is 0, 1, or 2;

q is 0, 1, 2, 3, or 4;

r is 0, 1, 2, or 3;

t is 0, 1, 2, or 3;

v is 0, 1, or 2;

and pharmaceutically acceptable salts and individual diastereomers thereof.

2. The compound of claim 1 wherein:

R$^1$ is selected from the group consisting of:
C$_1$–C$_{10}$ alkyl, aryl (C$_1$–C$_4$ alkyl)-, C$_3$–C$_6$ cycloalkyl (C$_1$–C$_4$ alkyl)-, (C$_1$–C$_4$ alkyl)-K—(C$_1$–C$_2$ alkyl)-, aryl (C$_0$–C$_2$ alkyl)-K—(C$_1$–C$_2$ alkyl)-, and (C$_3$–C$_7$ cycloalkyl)(C$_0$–C$_2$ alkyl)-K—(C$_1$–C$_2$ alkyl)-, where K is —O—, —S(O)$_m$—, —OC(O)—, —C(O)O— and the alkyl groups may be further substituted by 1 to 7 halogen, S(O)$_m$R$^2$, 1 to 3 OR$^2$ or C(O)OR$^2$ and aryl is phenyl, naphthyl, indolyl, pyridyl, benzothienyl, or benzofuranyl which may be further substituted by 1–2 C$_1$–C$_4$ alkyl, 1 to 2 halogen, 1 to 2 —OR$^2$, —S(O)$_m$R$^2$, or —C(O)OR$^2$;

R$^{1a}$ is hydrogen, or C$_1$–C$_6$ alkyl;

R$^2$ is selected from the group consisting of:
hydrogen, C$_1$–C$_6$ alkyl, and C$_3$–C$_7$ cycloalkyl and where two C$_1$–C$_6$ alkyl groups are present on one atom they may be optionally joined to form a C$_4$–C$_7$ cyclic ring optionally including oxygen, sulfur or NR$_{3a}$;

R$^{2a}$ is hydrogen, or C$_1$–C$_6$ alkyl;

R$^3$ is hydrogen or phenyl optionally substituted in the ortho position by a C$_1$–C$_6$ alkyl group, —NHSO$_2$CF$_3$, —(CH$_2$)$_r$ (1H-tetrazol-5-yl), —(CH$_2$)$_r$C(O)OR$^2$, or —(CH$_2$)$_r$C(O)N(R$^2$)(R$^6$);

R$^{3a}$ is hydrogen, or C$_1$–C$_4$ alkyl;

or R$^3$ and R$^{3a}$ together may form a spiro system of the formula:

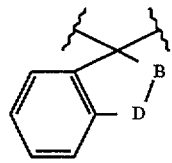

wherein B and D are independently selected from:
—C(R$^2$)(R$^8$)—, —C(O)—, —O—, —S(O)$_m$—, and —NR$^8$—, provided that if one of B or D is —O—, —S(O)$_m$—, and —NR$^8$—, then the other of B and D is not —O—, —S(O)$_m$—, or —NR$^8$—, R$^4$ and R$^5$ are independently hydrogen, C$_1$–C$_6$ alkyl, or substituted C$_1$–C$_6$ alkyl where the substituents are selected from: 1 to 5 halo, 1 to 3 hydroxyl, —S(O)$_m$ (C$_1$–C$_6$ alkyl), and phenyl;

R$^6$ is hydrogen, C$_1$–C$_6$ alkyl, or (CH$_2$)$_v$aryl, wherein the alkyl and (CH$_2$)$_v$ groups may be optionally substituted by 1–2 —O(R$^2$), —S(O)$_m$R$^2$, 1H-tetrazol-5-yl, —C(O)OR$^2$, —C(O)N(R$^2$)(R$^2$), —SO$_2$N(R$^2$)(R$^2$), or —N(R$^2$)C(O)N(R$^2$)(R$^2$), and where aryl is selected from: phenyl, naphthyl, quinolinyl, pyridyl, 1H-tetrazol-5-yl, triazolyl, imidazolyl, thiazolyl, pyrazolyl, thiadiazolyl, imidazolone-1-yl, oxadiazolyl, benzimidazol-2-yl, triazolinone-yl, and wherein the aryl is optionally substituted with 1 or 2 halogen, —R$^2$, —OR$^2$ or —NR$^2$R$^2$;

A is:

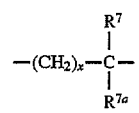

where x is 0, or 1;

R$^7$ and R$^{7a}$ are independently hydrogen C$_1$–C$_6$ alkyl, trifluoromethyl, phenyl, substituted C$_1$–C$_6$ alkyl where the substituents are imidazolyl, phenyl, indolyl, p-hydroxyphenyl, —OR$^2$, —S(O)$_m$R$^2$, —C(O)OR$^2$, C$_5$–C$_7$ cycloalkyl, —N(R$^2$)(R$^2$), —C(O)N(R$^2$)(R$^2$); or R$^7$ and R$^{7a}$ can independently be joined to one of R$^4$ or R$^5$ to form alkylene bridges between the terminal nitrogen and the alkyl portion of R$^7$ or R$^{7a}$ groups to form 5 or 6 membered rings; or R$^7$ and R$^{7a}$ can be joined to one another to form a C$_3$ cycloalkyl;

R$^8$ is independently selected from the group consisting of:
hydrogen, C$_1$–C$_6$ alkyl, —(CH$_2$)$_r$OR$^6$, —(CH$_2$)$_2$C(O)OR$^6$, —(CH$_2$)$_r$C(O)N(R$^2$)(R$^6$), —(CH$_2$)$_r$C(O)N(R$^2$)R$^2$), —(CH$_2$)$_r$N(R$^2$)C(O)R$^6$, —(CH$_2$)$_r$N(R$^2$)C(O)N(R$^2$)(R$^6$), —(CH$_2$)$_r$N(R$^2$)C(O)N(R$^2$)R$^6$), —(CH$_2$)$_r$R$^6$, —(CH$_2$)$_r$S(O)$_m$R$^6$, —(CH$_2$)$_r$SO$_2$N(R$^2$)(R$^6$), —(CH$_2$)$_r$SO$_2$N(R$^2$)(R$^2$), and —(CH$_2$)$_r$N(R$^2$)SO$_2$N(R$^2$)(R$^6$);

X is selected from the group consisting of:
hydrogen, —(CH$_2$)$_q$C(O)N(R$^2$)(R$^6$), —(CH$_2$)$_q$C(O)OR$^6$, —(CH$_2$)$_q$N(R$^6$)C(O)R$^6$, and —(CH$_2$)$_q$N(R$^6$)SO$_2$R$^6$;

Y is selected from the group consisting of:
hydrogen, C$_1$–C$_8$ alkyl, —(CH$_2$)$_t$phenyl, —(CH$_2$)$_t$pyridyl, and —(CH$_2$)$_t$thiazolyl;

m is 0, 1, or 2;

q is 0 or 1;

r is 0, 1, 2, or 3;

t is 0 or 1;

v is 0, 1, or 2;

and pharmaceutically acceptable salts and individual diastereomers thereof.

3. The stereospecifically defined compound of claim 1 of the formula:

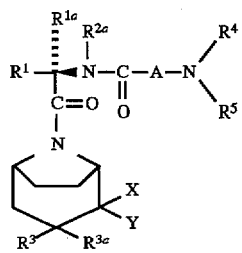

wherein R$^1$, R$^{1a}$, R$^{2a}$, R$^3$, R$^{3a}$, R$^4$, R$^5$, A, X, and Y are as defined in claim 1.

4. A compound which is selected from the group consisting of:

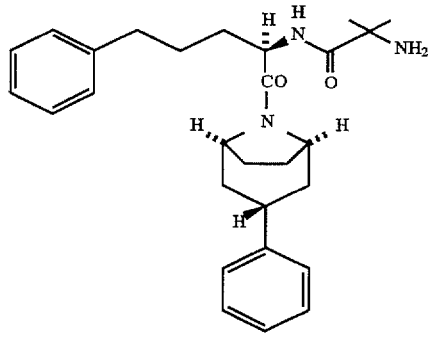
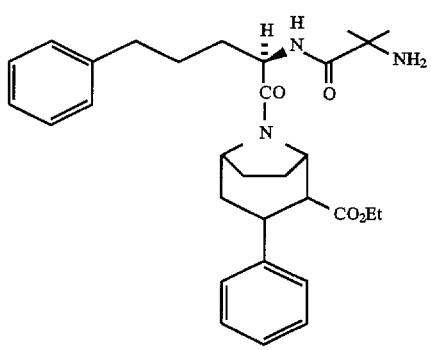
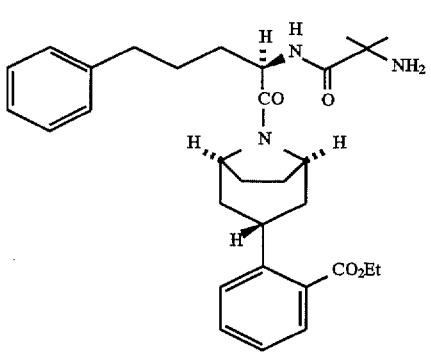
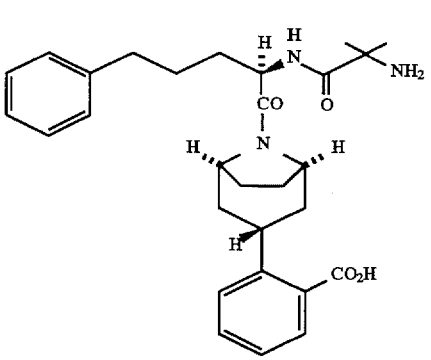
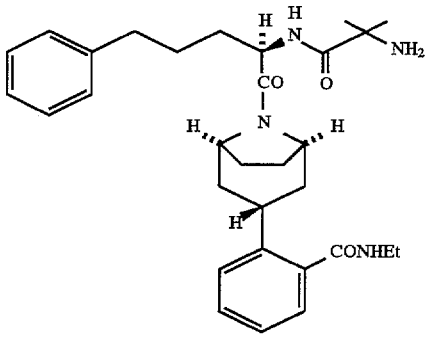
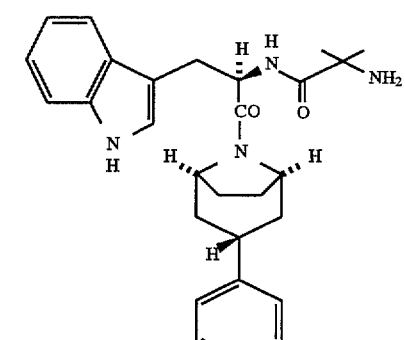
and their pharmaceutically acceptable salts and individual diasteromers thereof, where not otherwise specified.
5. A method for increasing levels of endogenous growth hormone in a human or an animal which comprises administering to such human or animal an effective amount of a compound of claim 1.
* * * * *